(12) United States Patent
Henry et al.

(10) Patent No.: US 8,636,701 B2
(45) Date of Patent: Jan. 28, 2014

(54) MEDICAL ARTICLE SECUREMENT SYSTEM

(75) Inventors: Adam S. Henry, Oceanside, CA (US); Clifford A. Wright, San Diego, CA (US); Tom Lorenzana, Spring Valley, CA (US); Robert F. Eisele, Carlsbad, CA (US); Thomas Jackson, La Jolla, CA (US)

(73) Assignee: Venetec International, Inc., Covington, GA (US)

( * ) Notice: Subject to any disclaimer, the term of this patent is extended or adjusted under 35 U.S.C. 154(b) by 306 days.

(21) Appl. No.: 12/765,751

(22) Filed: Apr. 22, 2010

(65) Prior Publication Data

US 2011/0264050 A1    Oct. 27, 2011

(51) Int. Cl.
*A61M 5/32* (2006.01)

(52) U.S. Cl.
USPC ............................ 604/178; 604/174; 604/177

(58) Field of Classification Search
USPC .......................................... 604/174, 177–180
See application file for complete search history.

(56) References Cited

U.S. PATENT DOCUMENTS

| | | | |
|---|---|---|---|
| 3,782,383 A | | 1/1974 | Thompson et al. |
| 5,069,206 A | * | 12/1991 | Crosbie ..................... 128/207.17 |
| 5,382,239 A | | 1/1995 | Orr et al. |
| 5,470,321 A | | 11/1995 | Forster et al. |
| 5,916,200 A | | 6/1999 | Eppley et al. |
| 6,523,231 B1 | | 2/2003 | Lassiter |
| 6,972,003 B2 | | 12/2005 | Bierman et al. |
| 7,014,627 B2 | | 3/2006 | Bierman |
| 7,776,017 B2 | | 8/2010 | Ponzi et al. |
| 2004/0204685 A1 | | 10/2004 | Wright et al. |
| 2005/0192539 A1 | | 9/2005 | Bierman et al. |
| 2006/0025723 A1 | | 2/2006 | Ballarini |
| 2006/0135944 A1 | | 6/2006 | Bierman |
| 2007/0249980 A1 | | 10/2007 | Carrez et al. |

FOREIGN PATENT DOCUMENTS

| | | |
|---|---|---|
| GB | 2472268 | 2/2011 |
| WO | WO 00/48658 | 8/2000 |
| WO | WO 2004/016309 | 2/2004 |
| WO | WO 2004/022140 | 3/2004 |
| WO | WO 2009/055739 | 4/2009 |
| WO | WO 2011/133818 | 10/2011 |

OTHER PUBLICATIONS

International Search Report dated Apr. 10, 2009 for International Application No. PCT/US2007/81846.
International Search Report dated Dec. 29, 2008 for International Application No. PCT/US2008/081216.
International Search Report and Written Opinion dated Jun. 29, 2011 for PCT Application No. PCT/US2011/033499.

* cited by examiner

*Primary Examiner* — Emily Schmidt
*Assistant Examiner* — Bradley G Thomas, Jr.
(74) *Attorney, Agent, or Firm* — Knobbe, Martens, Olson & Bear, LLP

(57) ABSTRACT

A medical article securement device holds a medical article such as a catheter in position upon the body of a patient and at least inhibits longitudinal movement of the medical article. The securement device includes a retainer, a pair of hinged actuators, and a pair of engagement members coupled with the hinged actuators. Movement of the actuators causes the engagement members to grip at least a portion of a medical article placed within the retainer so as to inhibit longitudinal movement of the medical article with respect to the retainer. The shape of the retainer inhibits lateral and transverse movement of the medical article with respect to a patient's skin.

21 Claims, 27 Drawing Sheets

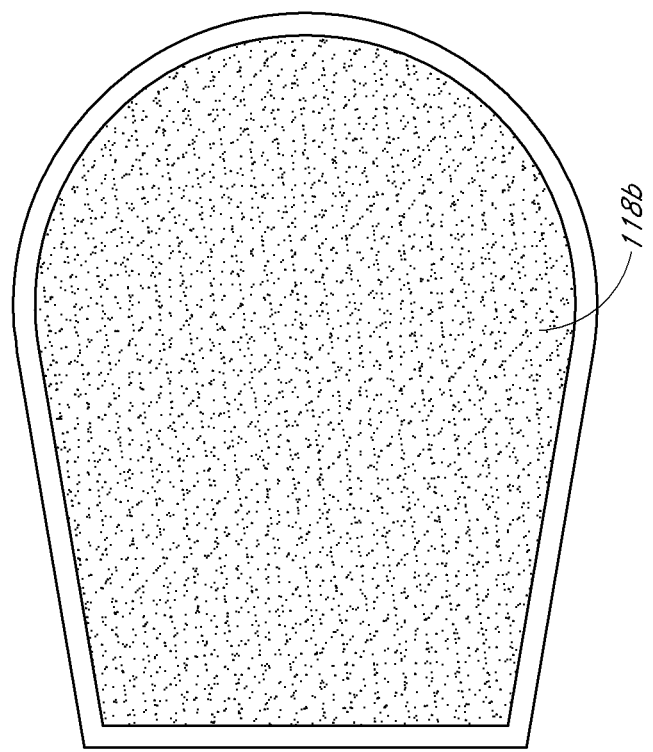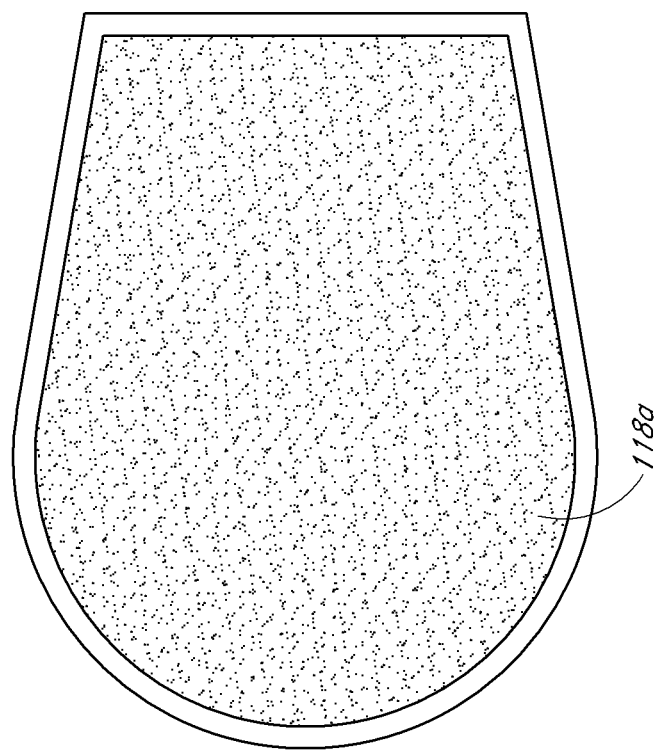
FIG. 21

MEDICAL ARTICLE SECUREMENT SYSTEM

BACKGROUND OF THE INVENTION

1. Field of the Invention

This invention relates to a securement system used to attach a catheter or other medical article to a patient.

2. Description of the Related Art

It is often necessary to introduce fluids and liquid medications directly into a blood vessel of a patient. Various types of medical articles, such as catheters, are often used in combination with connectors and syringes. A catheter is essentially a tube inserted through an incision in the skin into a blood vessel in the patient's body, generally without surgery. A simple intravenous (IV) line is usually acceptable for introduction of fluids and liquid medications into a blood vessel for short term general use. IV lines are typically inserted into a patient's arm by inserting a catheter or some other medical article, containing a needle, which pierces the skin, into a blood vessel. The needle is removed and discarded, while the medical article remains in the blood vessel.

It is important to minimize movement of the inserted medical article. If the medical article is not properly secured in place, it may be inadvertently displaced from its intended location. Consequently, medication delivered through the IV line may be released at an incorrect position. Furthermore, repeated back and forth movement of the medical article, or positioning, can cause irritation of the blood vessel, disrupt proper introduction of medications to the patient, and increase the potential for bleeding or infection at the medical article insertion site. If extensive movement occurs, the IV line could even come out of the patient, interrupting delivery of medication and requiring re-insertion, often with hospitalization.

In the past, medical articles, such as catheters, were typically taped into place on the patient's skin. However, taping is time consuming and labor intensive. Tape also collects bacteria and must be frequently removed and replaced. More importantly, taping is not necessarily effective for securing a medical article in place on a patient. Sutures have also been used to attach medical articles to patients. With sutures, the medical article is stitched onto the skin. Sutures, however, can also be a source of infection, can cause pain and inflammation, and can make it more difficult to clean around the insertion site. Sutures also require time and skill to apply, and can cause scarring.

SUMMARY OF THE INVENTION

In accordance with one aspect of the devices and techniques described herein, a retainer is provided. The retainer includes a body member having a channel and one or more openings disposed in the body member. The channel can have a longitudinal axis and the channel can receive at least a portion of a medical article. The retainer also has one or more base portions coupled with the body member. The base portions extend laterally from the body member and support the body member. The retainer also includes one or more actuators that are coupled with the one or more base portions and move between a first position and a second position. At least a portion of each actuator is disposed in the channel when the actuator is in the first position and the portion is removed from the channel when the actuator is in the second position.

In accordance with another aspect of the device, a retainer for securing a medical article relative to a patient is provided. The retainer includes a body member, a first base portion, and a first actuator. The body member forms a channel having a first opening in a lateral side of the body member. The channel has a longitudinal axis and is configured to receive at least a portion of the medical article with at least a portion of the medical article being aligned with the first opening. The first base portion is coupled with the body member and extends laterally therefrom at a location below the longitudinal axis of the channel. The first actuator is movably coupled with the first base portion and moves relative to the body member between at least a first position and a second position. At least a portion of the first actuator is received within the first opening when the first actuator is in the first position.

In accordance with another aspect of the device, a retainer for securing a medical article relative to a patient is provided. The retainer includes a body member, a base portion, an actuator, and an actuator stop. The body member forms a channel having a longitudinal axis and is configured to receive at least a portion of the medical article. The base portion is coupled with the body member and extends laterally therefrom at a location below the longitudinal axis of the channel. The actuator is movably coupled with the base portion and moves relative to the body member between at least a first position and a second position. The actuator stop is coupled with the base portion and selectively limits movement of the actuator relative to the body member and toward the second position. At least a portion of the actuator stop is movable so as to allow the actuator to move to the second position.

BRIEF DESCRIPTION OF THE DRAWINGS

FIG. 21 is a top view of the adhesive pads shown in FIG. 1.

DETAILED DESCRIPTION OF THE PREFERRED EMBODIMENTS

The following description and the accompanying figures, which describe and show the preferred embodiments, are made to demonstrate several possible configurations that a securement system can take to include various aspects and features of the invention. The illustrated embodiments are shown in use with an illustrative example of a medical article that includes a catheter hub and extension set nut. For example, embodiments of the retainer may be used with Smiths Medical AdvantIV and ProtectIV catheters. However, the securement system may be used with other catheter designs. The illustration of the securement device in this context is not intended to limit the disclosed aspects and features of the invention to the specified embodiments or to usage only with the illustrated medical article. Those of skill in the art will recognize that the disclosed aspects and features of the invention are not limited to any particular embodiment of a securement system, and securement systems, which include one or more of the inventive aspects and features herein described, can be designed for use with a variety of medical articles (or combinations of medical articles) of varying design. One skilled in the art may also find additional applications for the devices and systems disclosed herein.

Figure 1:
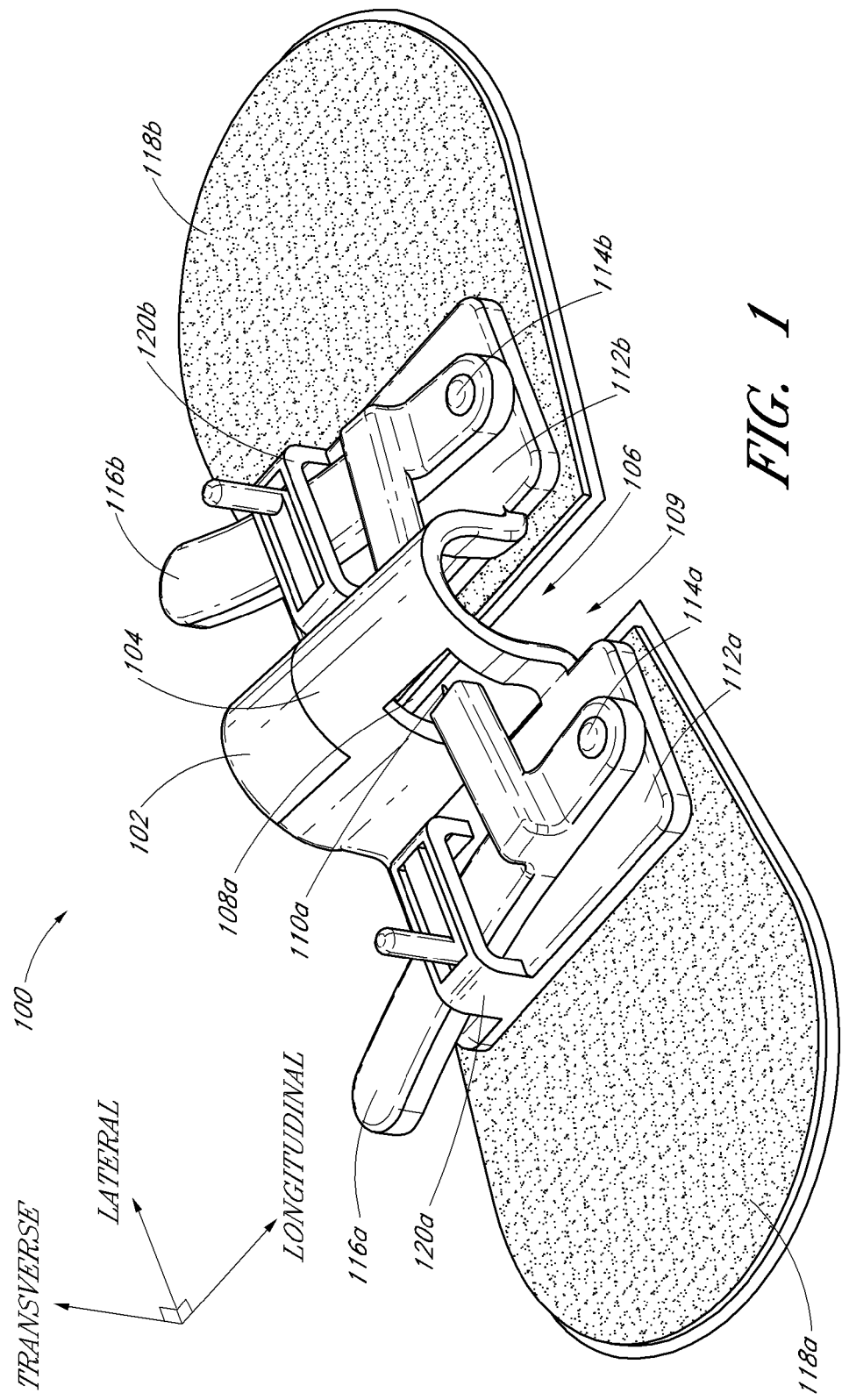
FIG. 1 is a perspective view of a securement system in accordance with an embodiment of the present invention.

To assist in the description of these components of the securement system, the following coordinate terms are used (see FIG. 1). A "longitudinal axis" is generally parallel to a portion of the medical article retained by the securement system, as well as parallel to the axis of a channel of the retainer, through which the medical article extends. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or connector fitting, and therefore is substantially synonymous with the term "longitudinal" as used herein. Also, the terms "proximal" and "distal", which are used to describe the present securement system, are used consistently with the description of the exemplary applications (i.e., the illustrative example of the use application). Thus, proximal and distal are used in reference to the center of the patient's body. The terms "upper," "lower," "top," "bottom," "underside," "upperside" and the like, which also are used to describe the present securement system, are used in reference to the illustrated orientation of the embodiment. For example, the term "upperside" is used to describe the portion of the retainer that is located above a lateral axis that passes through the axis of the channel. The term "underside" is used to describe the portion of the retainer that is located below a lateral axis that passes through the axis of the channel. Brief introductions to some of the features, which are common to the described embodiments of the securement systems, are now described.

The securement system described herein is especially adapted to arrest transverse, lateral, and/or longitudinal movement of a medical article, such as a catheter, as well as to stabilize and hold the medical article against the patient. As described below, retention mechanisms to accomplish these goals includes a pair of hinged actuators with engagement members configured to engage the medical article within the retainer. In some embodiments, the securement system is adapted to secure the medical article as close to the insertion site as possible, while also providing a low profile and maintaining a desired insertion angle, for example, 7 degrees between the needle and patient's skin. In other embodiments, the insertion angle may be above 0 degrees and below about 50 degrees. In some embodiments, the securement system is adapted to allow stable securement of a variety of medical articles of differing dimensions.

In some embodiments, a securement system generally includes a retainer and a pair of hinged actuators. The hinged actuators may include engagement members. The retainer includes a longitudinal channel configured to receive and secure at least a portion of a medical article. The longitudinal channel has lateral openings designed to provide access to the channel for the hinged actuators. The retainer also includes left and right anchor feet that are preferably disposed on the underside of the retainer at a position lower than the lateral openings. The bottom of the left and right anchor feet are attached to a pair of adhesive pads. The lower surfaces of the adhesive pads attach to the patient's skin. The left and right anchor feet can include actuator stops. The actuator stops may control the range of movement of the hinged actuators.

One of the hinged actuators is pivotally coupled to the left anchor foot and the other is pivotally coupled to the right anchor foot. The hinged actuators may pivot around pins extending from the left and right anchor feet. The actuators can be manipulated in order to pivot the engagement members into and out of the lateral openings to engage and disengage a medical article received within the channel. The actuators and the retainer thus cooperate to inhibit at least longitudinal movement of the medical article with respect to the retainer. With this construction, the retainer can hold the retained portion of the medical article in a secure and stable manner, close to the patient's skin, when the retained portion is positioned within the channel, while avoiding chafing or excoriating the skin.

With reference now to FIGS. 1-21 securement system 100 generally includes a retainer 104 and left and right hinged actuators 116a, 116b. The retainer 104 can comprise any suitable material offering the desired degree of rigidity (and flexibility) for each part, including, without limitation, a stiff but somewhat flexible plastic, such as a polycarbonate. The body of the retainer 104 includes a longitudinally-extending channel 106 which is configured to receive at least a portion of a medical article. The channel 106 can have a constant or variable cross section, such as a taper, along a portion or all of its length, and can be configured to roughly match the cross section of the portion of the medical article which it is adapted to retain. The channel 106 can extend through an arc of greater than 180 degrees, so as to provide a degree of snap-fit between the retainer 104 and a medical article.

The channel 106 has a longitudinal opening 109 located on the underside of the retainer 104, to allow ingress or egress of the medical article. The medical article is installed or removed from the underside of the retainer 104 via this opening 109. Such an arrangement allows the medical provider to align at least a portion of a medical article within the retainer 104 prior to fixing the retainer to the patient's skin. The body of the retainer 104 further includes lateral openings 108a, 108b. The lateral openings 108a, 108b allow ingress and egress of at least a portion of the hinged actuators 116a, 116b into the channel 106.

The illustrated retainer 104 includes left and right anchor feet 112a, 112b disposed on anchor pads 118a, 118b. The feet 112a, 112b may be disposed at a position lower than the opening 109, so as to limit or prevent contact of the retained portion of the medical article with the skin of the patient. The feet 112a, 112b are spaced apart so as to allow ingress and egress of a medical article therebetween. The retainer 104 and the hinged actuators 116a, 116b may be pivotally connected. Each hinged actuator 116a, 116b may pivot around a pin 114a, 114b extending from the left and right anchor feet 112a, 112b.

Hinged actuators 116a, 116b include engagement members 110a, 110b. In one embodiment the engagement members 110a, 110b include a plurality of spikes. In another engagement, each engagement member 110a, 110b includes one spike or barb. In some embodiments, the engagement members 110a, 110b are configured to arrest transverse, lateral, and/or longitudinal movement of a medical article positioned within channel 106.

Pins 114a, 114b may extend in a transverse direction from the left and right anchor feet 112a, 112b. The hinged actuators 116a, 116b may be manipulated around pins 114a, 114b by the movement of the actuators 116a, 116b. According to one embodiment, movement of the actuators 116a, 116b pivots the actuators around pins 114a, 114b and into and out of lateral openings 108a, 108b. In another embodiment, movement of the actuators 116a, 116b pivots engagement members 110a, 110b into and out of the lateral openings 108a, 108b to engage a medical article.

In some embodiments, left and right anchor feet 112a, 112b include actuator stops 120a, 120b. The actuator stops 120a, 120b limit the movement of left and right hinged actuators 116a, 116b around left and right pins 114a, 114b. The anchor feet 112a, 112b can have adhesive pads 118a, 118b disposed on the undersides so as to allow attachment of the feet 112a, 112b to the skin of a patient.

Each adhesive pad 118a, 118b desirably comprises a laminate structure with an upper plastic, paper or foam layer (e.g., closed-cell polyethylene foam) and a lower adhesive layer. The lower adhesive layer constitutes a lower surface of the adhesive pad. The lower surface desirably is a medical-grade adhesive and can be either diaphoretic or nondiaphoretic, depending upon the particular application. Such foam with an adhesive layer is available commercially from Avery Dennison of Painsville, Ohio. While not illustrated, the adhesive pads 118a, 118b can include suture holes in addition to the adhesive layer to further secure the adhesive pad to the patient's skin.

In other variations, a hydrocolloid adhesive or zinc oxide-based adhesive can advantageously be used upon the adhesive pads 118a, 118b for attaching the adhesive pads 118a, 118b to the skin of the patient. The hydrocolloid or zinc oxide-based adhesive can be used either alone or in combination with another medical grade adhesive (e.g., in combination with the adhesive available from Avery Dennison). Hydrocolloid and zinc oxide-based adhesives have less of a tendency to excoriate the skin of a patient when removed. This can be particularly important for patients whose skin is more sensitive or fragile, such as neonates and those with a collagen deficiency or other skin related condition.

In another variation, each adhesive pad 118a, 118b comprises a laminate structure with an upper woven layer and a lower adhesive layer. The upper layer can be polyester or other suitable polymer or textile materials. One particular suitable material is woven polyester available commercially under the name "Tricot" from Tyco. The lower adhesive layer constitutes the lower surface of the adhesive pad. The lower surface desirably is a medical-grade adhesive and can be either diaphoretic or nondiaphoretic, depending upon the particular application.

A surface of the upper foam layer constitutes an upper surface of the adhesive pads 118a, 118b. The upper surface can be roughened by corona-treating the foam with a low electric charge. The roughened or porous upper surface can improve the quality of the adhesive joint between the anchor feet 112a, 112b and the adhesive pads 118a, 118b. In a further variation, the flexible adhesive pad can comprise an upper paper or other woven or nonwoven cloth or plastic layer in lieu of a roughened upper foam surface.

A removable paper or plastic release liner desirably covers the adhesive lower surface before use. The liner preferably resists tearing and desirably is divided into a plurality of pieces to ease attachment of the pad to a patient's skin. The liner comprises a folded over portion to define a pull tab. The pull tab can be utilized to remove the paper or plastic release liner from their adhesive lower surface before use. A medical provider uses the pull tab by grasping and pulling on it so that the liner is separated from the lower surface. The pull tab overcomes any requirement that the medical provider pick at a corner edge or other segment of the liner in order to separate the liner from the adhesive layer.

The pull tab of course can be designed in a variety of configurations. For example, the pull tab can be located along a center line of the adhesive pad; or alternatively, the pull tab can be located along any line of the adhesive pad in order to ease the application of the anchor pad onto the patient's skin at a specific site. For example, an area of a patient's skin with an abrupt bend, such as at a joint, can require that the pull tab be aligned toward one of the lateral ends of the adhesive pad rather than along the center line.

The retainer 104 also includes a removable tab 102. Removable tab 102 may be disposed in the top of retainer 104. Removable tab 102 may be configured to allow access to a medical article retained within retainer 104 when the removable tab 102 is removed from the retainer 104. Also, the removable tab 102 may be configured to fit within an opening on retainer 104 with the opening capable of receiving an outwardly extending member of a medical article when the removable tab 102 is removed from the retainer 104.

Figure 2:
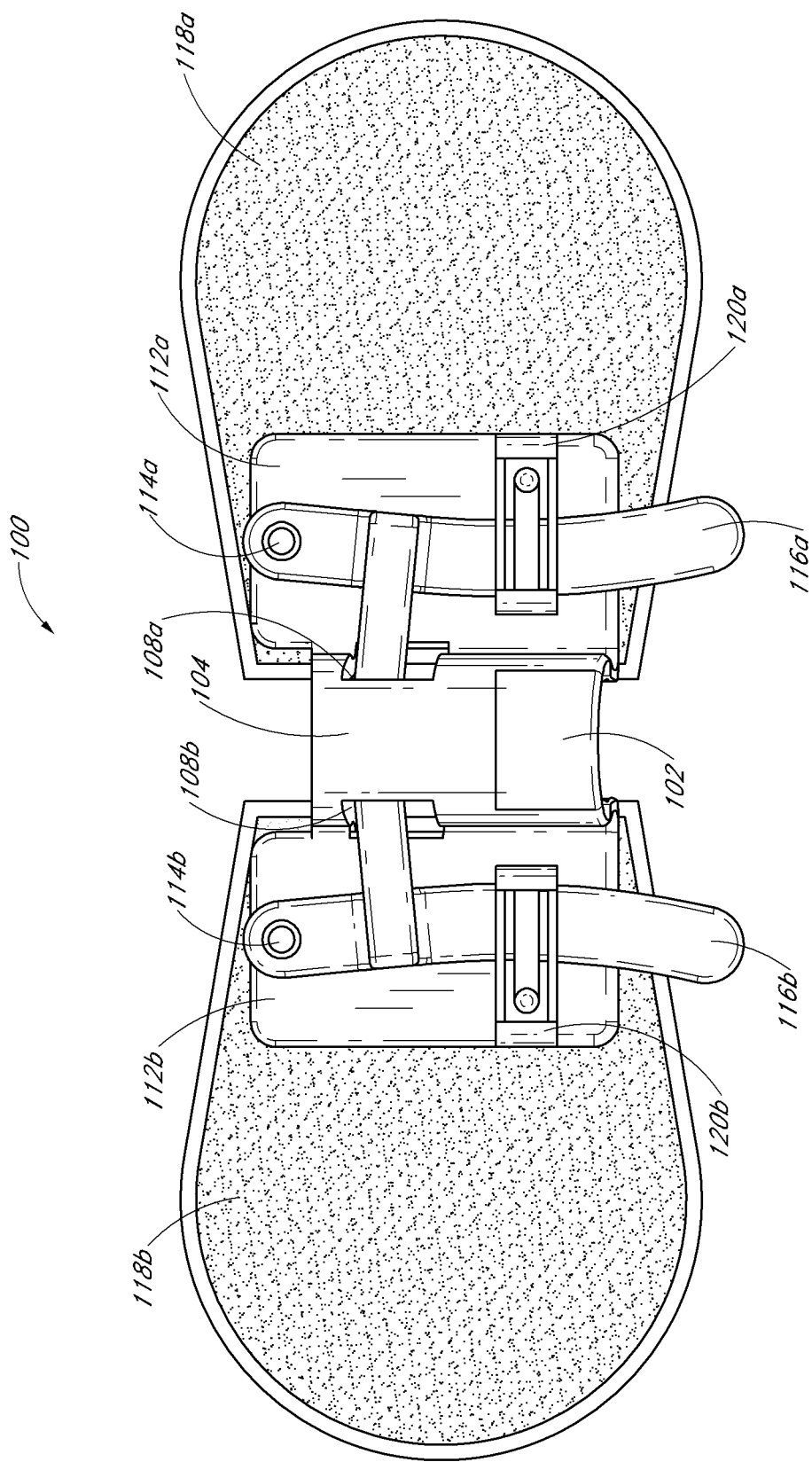
FIG. 2 is a top view of the securement system shown in FIG. 1. The pads shown in FIGS. 1 and 2 are omitted from some of the figures described below to more clearly illustrate the other components of the securement system.
Figure 3:
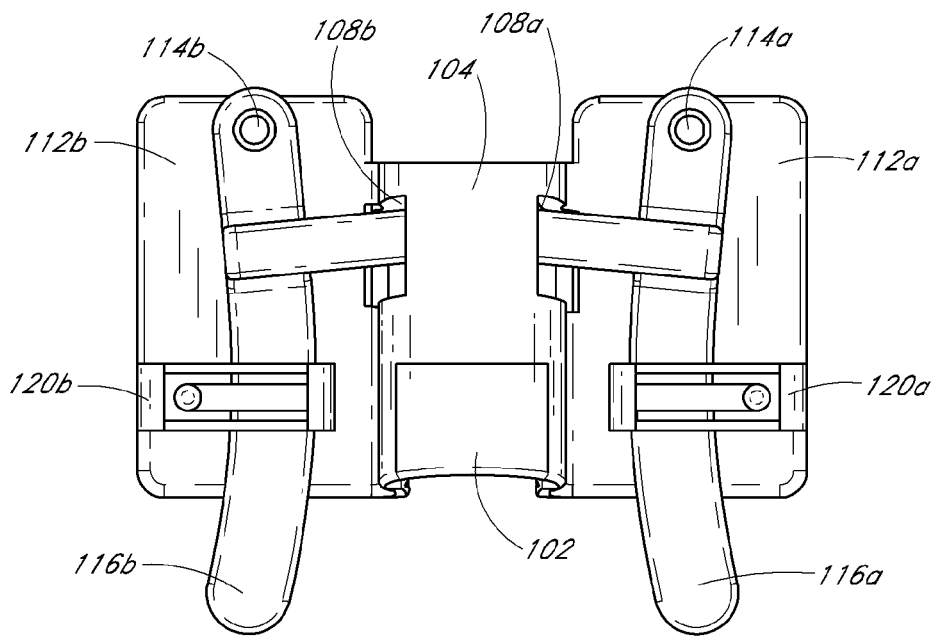
FIG. 3 is a top view of the securement system shown in FIG. 1.
Figure 4:
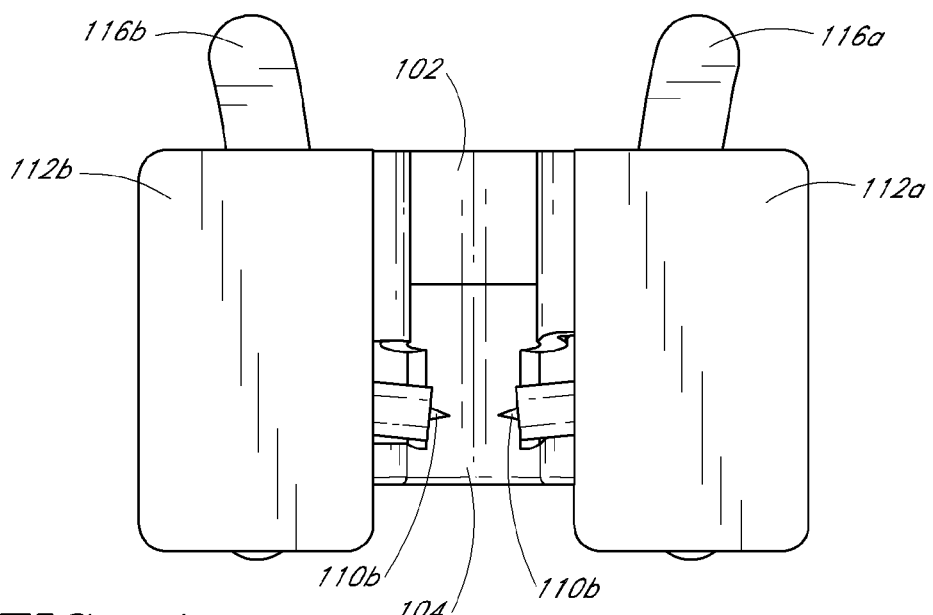
FIG. 4 is a bottom view of the securement system shown in FIG. 1.

FIGS. 2 and 3 are top views of the securement system 100 with and without the anchor pads shown, respectively. FIG. 4 is a bottom view of the securement system 100 without the anchor pads shown. As can be seen in FIG. 4, the engagement members 110a, 110b may extend from the hinged actuators 116a, 116b such that manipulation of the actuators 116a, 116b pivots the engagement members 110a, 110b.

Figure 5:
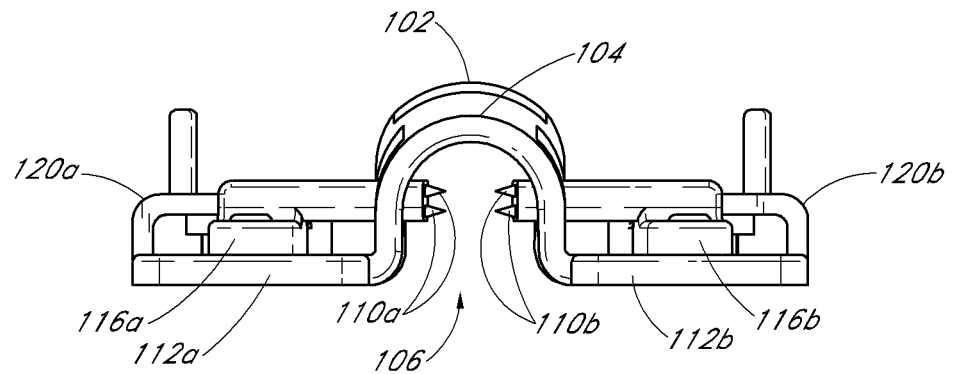
FIG. 5 is a front view of the securement system shown in FIG. 1.
Figure 6:
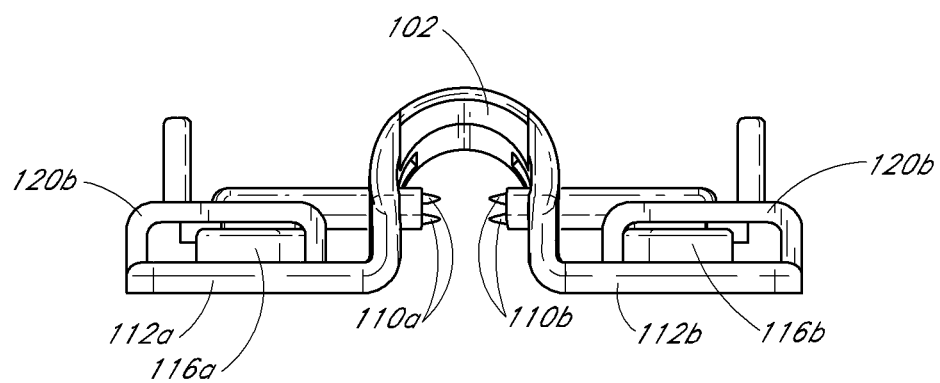
FIG. 6 is a rear view of the securement system shown in FIG. 1.

FIGS. 5 and 6 are front and rear views, respectively, of the securement system 100 shown without anchor pads. As shown in FIGS. 5 and 6, the engagement members 110a, 110b may include a plurality of spikes, barbs, or tapered points configured to engage a medical article.

Figure 7:
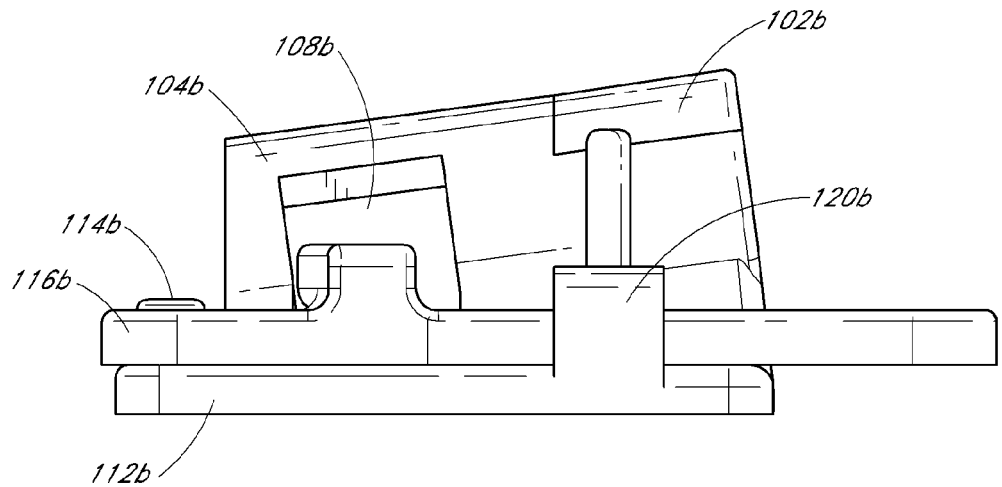
FIGS. 7 and 8 are side views of the securement system shown in FIG. 1.
Figure 8:
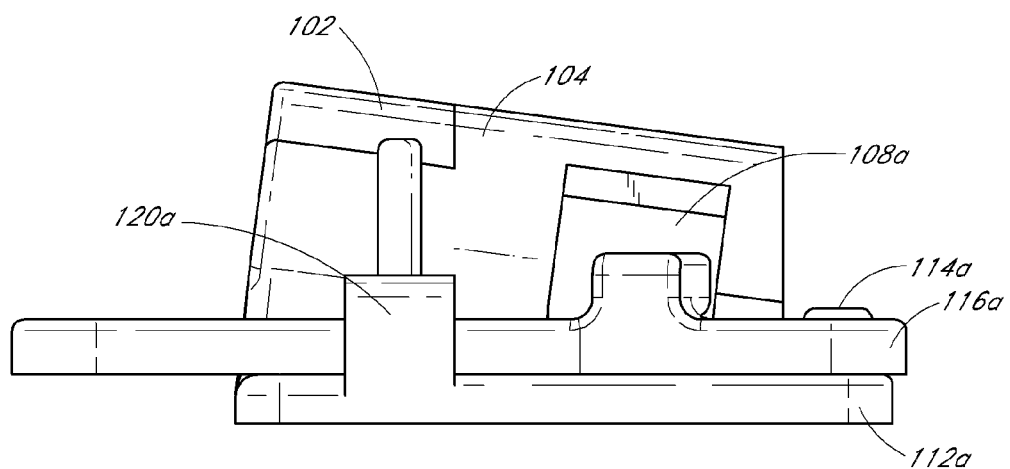

FIGS. 7 and 8 are left and right side views, respectively, of the securement system 100 shown without anchor pads. As can be seen by FIGS. 7 and 8, the retainer 104 may be angled relative to the anchor feet 112a, 112b to provide a desired insertion angle for a medical article.

Figure 9:
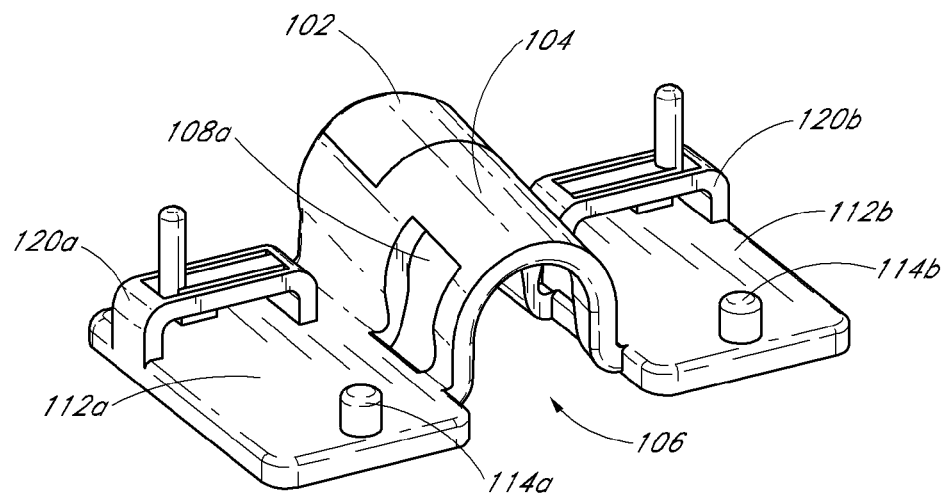
FIG. 9 is a perspective view of the retainer shown in FIGS. 1-8.
Figure 10:
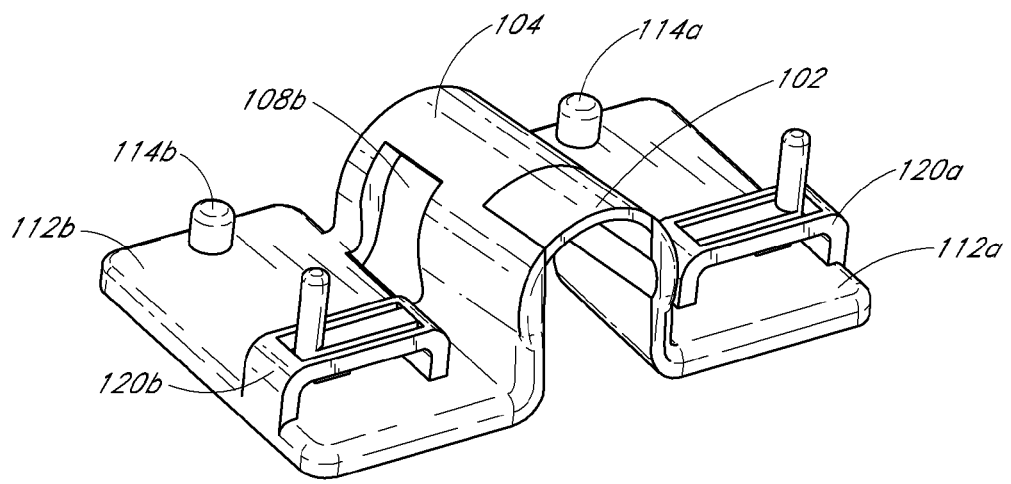
FIG. 10 is a rear perspective view of the retainer shown in FIG. 9.
Figure 11:
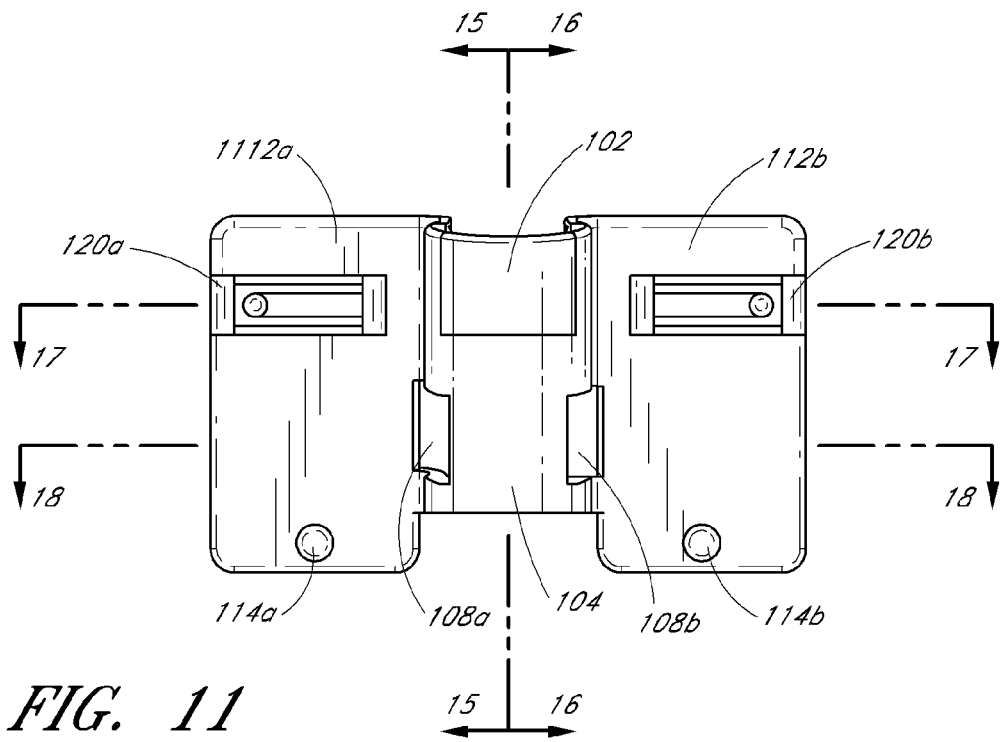
FIG. 11 is a top view of the retainer shown in FIG. 9.
Figure 12:
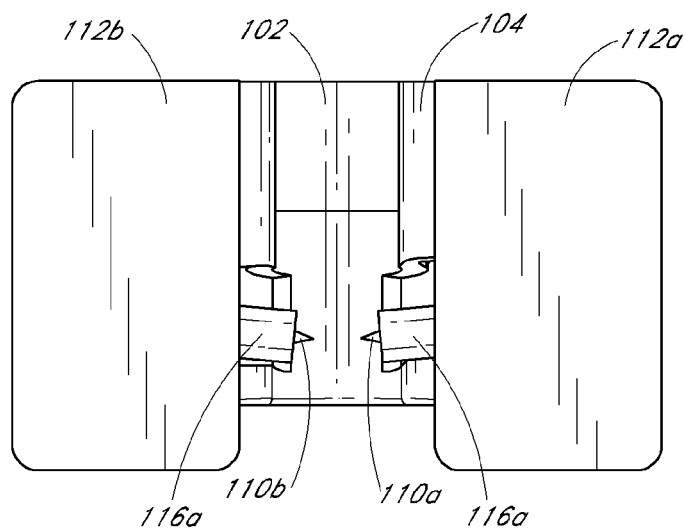
FIG. 12 is a bottom view of the retainer shown in FIG. 9.
Figure 13:
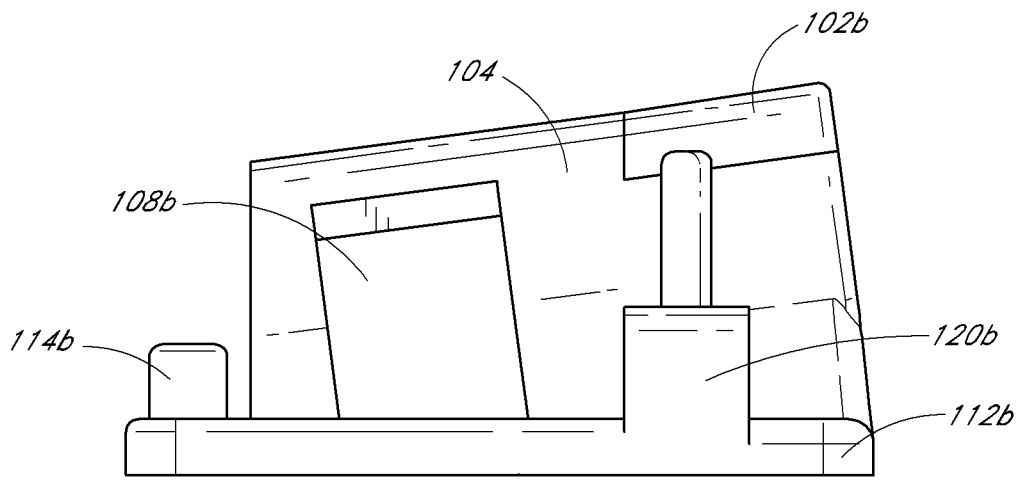
FIGS. 13 and 14 are side views of the retainer shown in FIG. 9.
Figure 14:
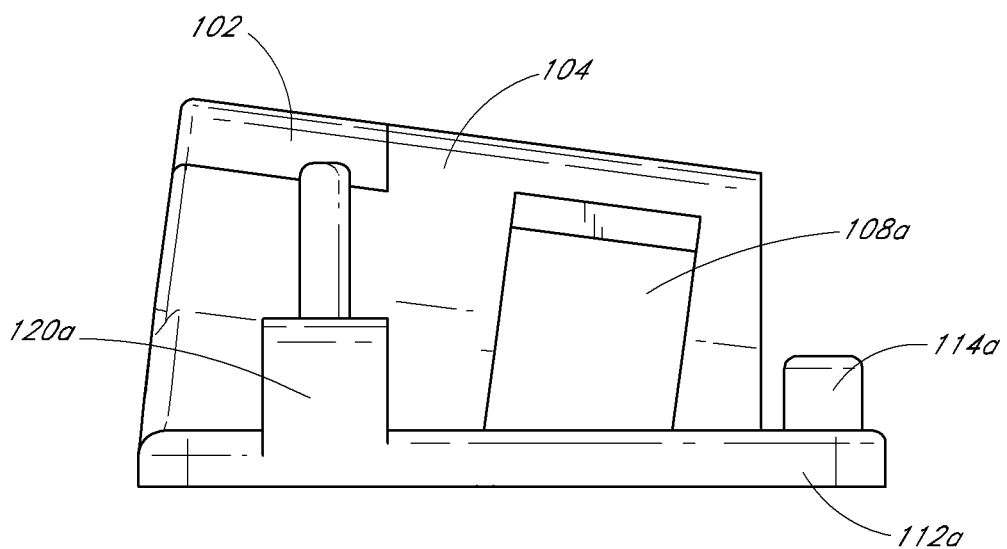

FIGS. 9 and 10 show front and rear perspective views, respectively, of the retainer 104 shown without anchor pads and hinged actuators. FIGS. 11 and 12 show top and bottom views, respectively, of the retainer 104 without anchor pads and hinged actuators. FIGS. 13 and 14 are right and left side views, respectively, of the retainer 104 without anchor pads and hinged actuators.

Figure 15:
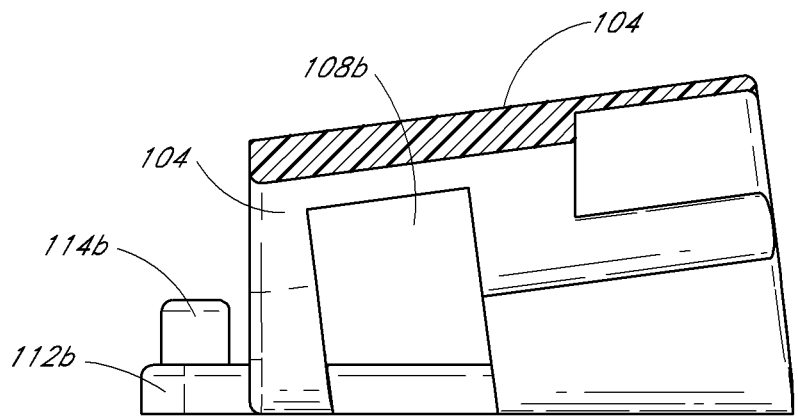
FIG. 15 is a cross-sectional view of the retainer shown in FIG. 11 taken along line 15-15.
Figure 16:
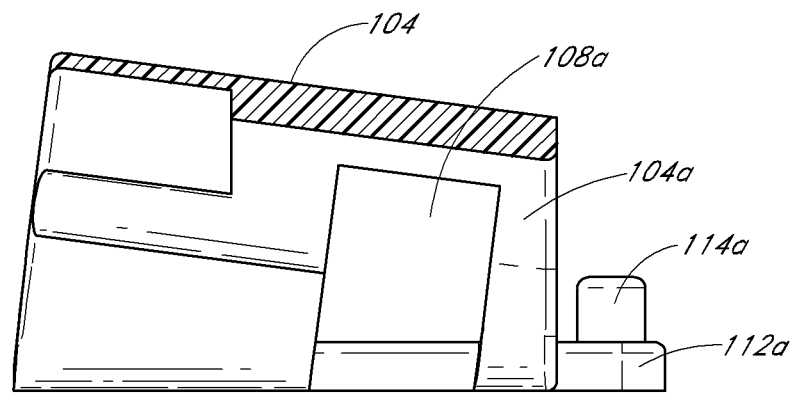
FIG. 16 is a cross-sectional view of the retainer shown in FIG. 11 taken along line 16-16.
Figure 17:
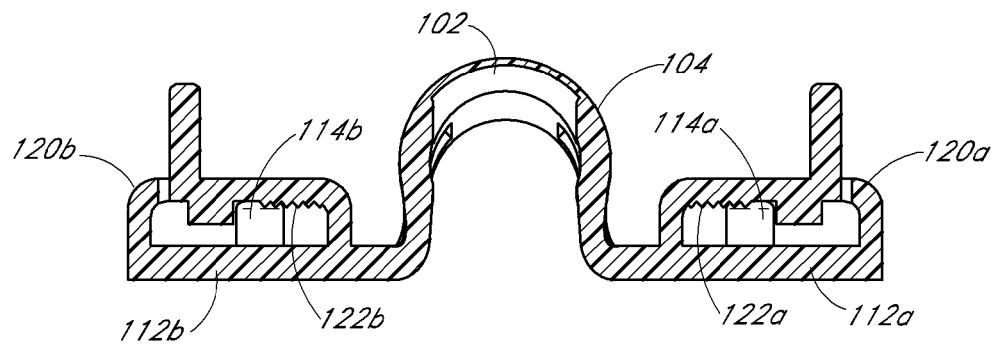
FIG. 17 is a cross-sectional view of the retainer shown in FIG. 11 taken along line 17-17.
Figure 18:
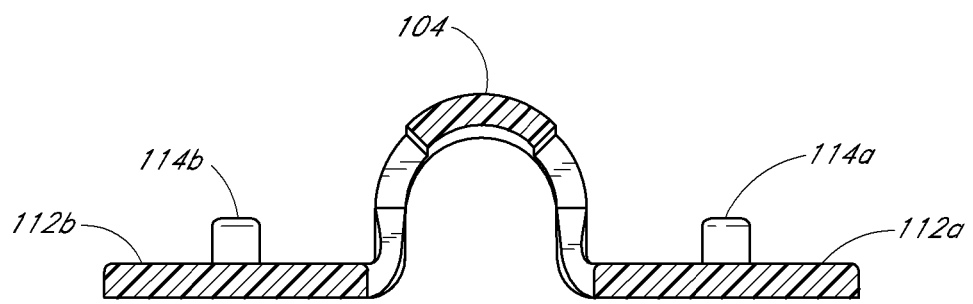
FIG. 18 is a cross-sectional view of the retainer shown in FIG. 11 taken along line 18-18.

FIGS. 15 and 16 are cross-sectional views of the retainer 104 taken along lines 15-15 and 16-16, respectively. FIGS. 17 and 18 are cross-sectional views of the retainer taken along lines 17-17 and 18-18, respectively. As can be seen in FIG. 17, the underside of actuator stops 120a, 120b may include engagement structure 122a, 122b. In some embodiments, the engagement structure 122a, 122b may include teeth. The engagement structure 122a, 122b may engage hinged actuators (not shown) in order to adjustably secure the position of the hinged actuators with respect to the retainer 104.

Figure 19:
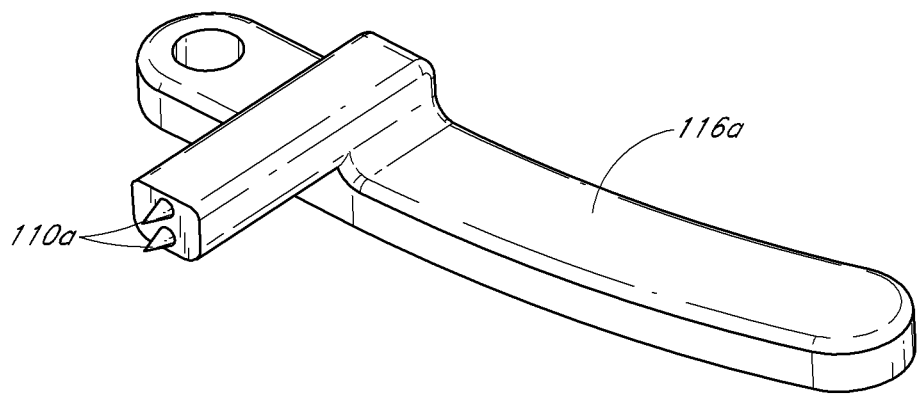
FIG. 19 is a perspective view of the right actuator shown in FIGS. 1-6.
Figure 20:
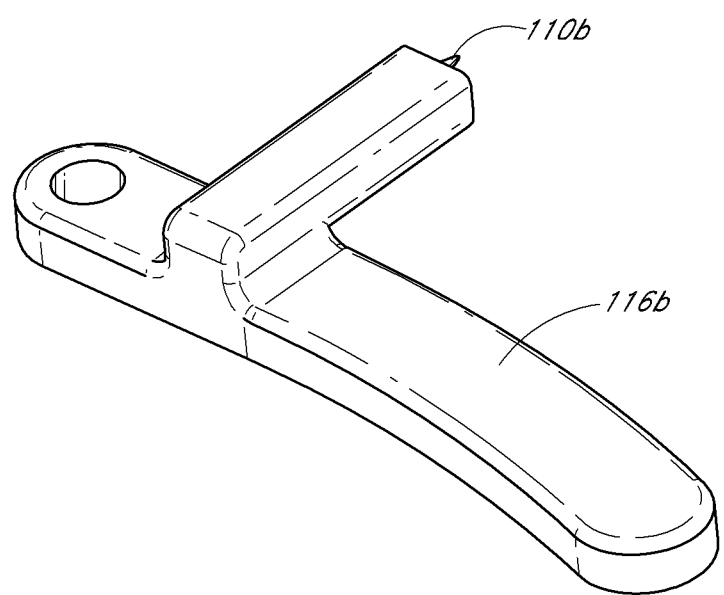
FIG. 20 is a perspective view of the left actuator shown in FIGS. 1-6.

FIGS. 19 and 20 are perspective views of the right and left actuators 116a, 116b, respectively. As shown, the engagement members 110a, 110b can include one or more spikes, barbs, or points. In other embodiments, the engagement members 110a, 110b can include other structures. FIG. 21 is a top view of the adhesive pads 118a, 118b shown in FIG. 1.

Figure 22:
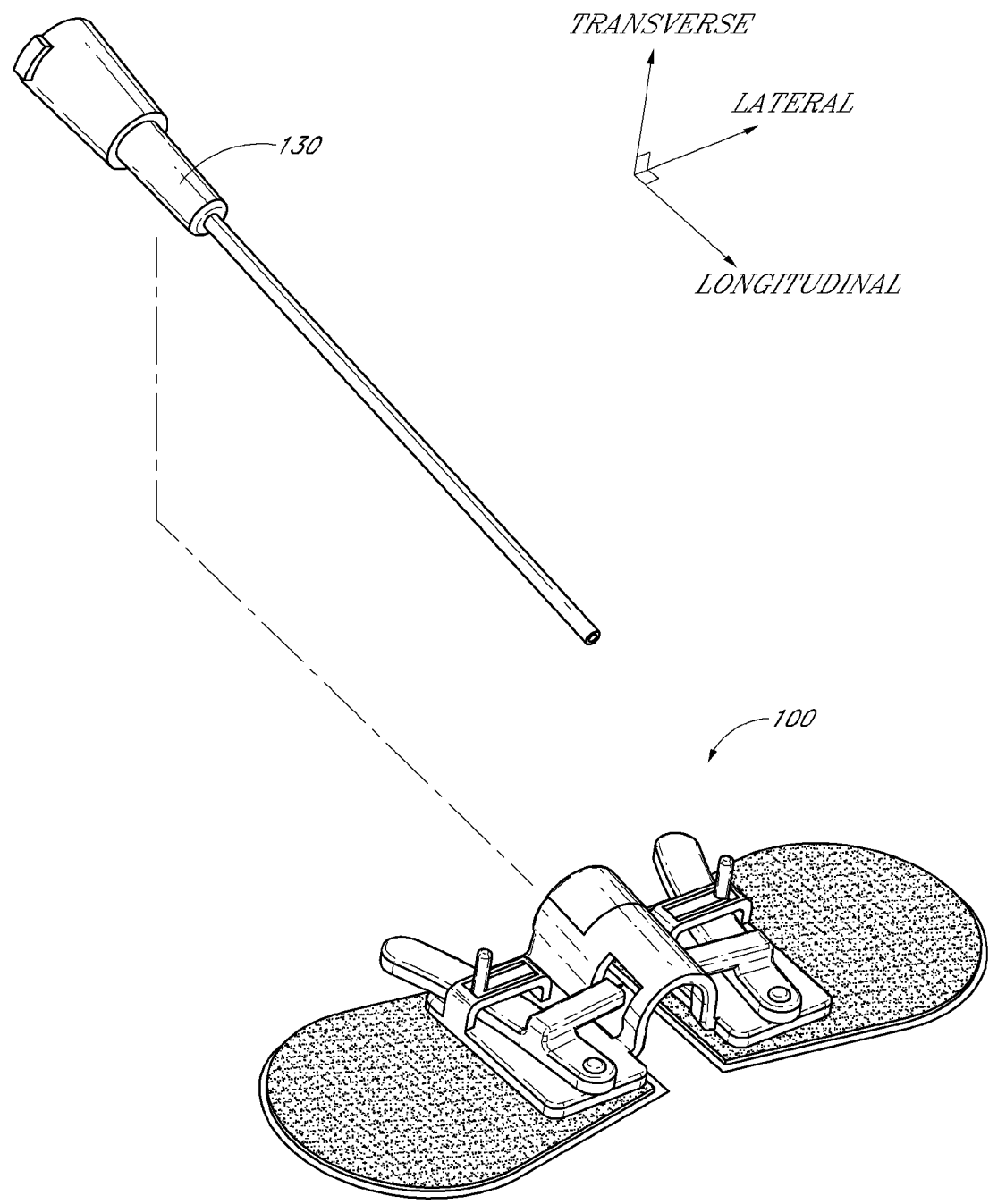
FIG. 22 is a perspective view of the securement system shown in FIG. 1 and a medical article.
Figure 23:
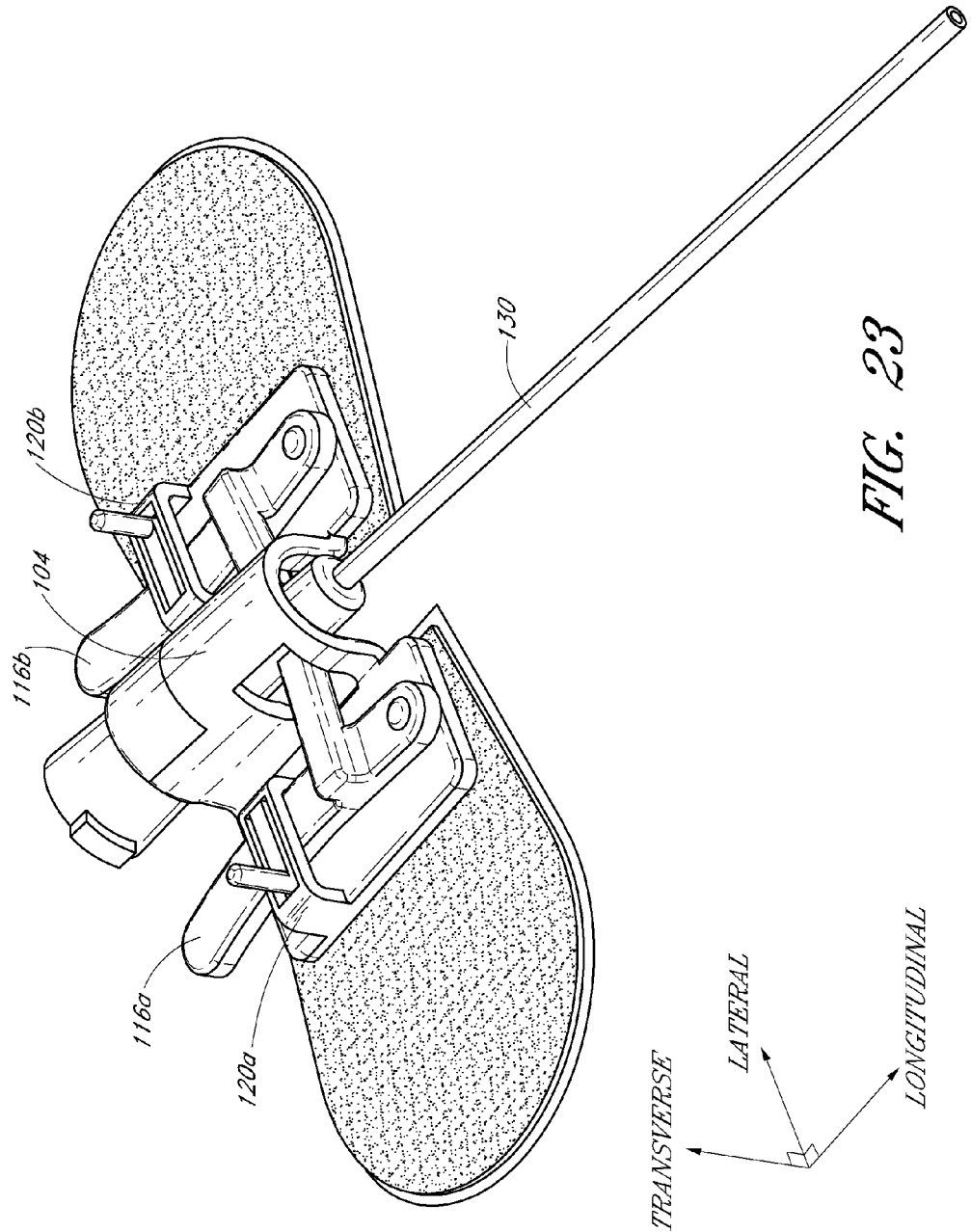
FIG. 23 is a perspective view of the securement system shown in FIG. 1 with a secured medical article.

Turning now to FIG. 22, the securement system 100 shown in FIG. 1 is illustrated with a medical article 130. In use, a medical professional may secure the medical article 130 relative to a patient's skin using the securement system 100. As can be seen in FIG. 23, a portion of the medical article 130 is received within the retainer 104 and the actuators 116a, 116b engage the medical article 130 to inhibit longitudinal, lateral, and transverse movement of the medical article 130 relative to the retainer 104. The actuator stops 120a, 120b can limit the movement of the actuators 116a, 116b between at least an open position and a closed position.

Turning to FIGS. 24-42, in an alternative embodiment, a securement system 200 includes a retainer 204 and left and right hinged actuators 216a, 216b. The top of retainer 204 may include an opening 244. The opening 244 may be configured to allow access to a medical article retainer within retainer 204 and/or to receive an outwardly extending member of a retained medical article. The retainer 204 is gripped by a securement band 240. Securement band 240 is configured to grip retainer 204 and maintain the shape of retainer 204 when at least a portion of the medical article is retained within the retainer 204. The securement band 240 may be metal or any other material capable of gripping or compressing the retainer 240. As shown in FIG. 32A, the retainer 204 may include openings 250 capable of receiving the ends of securement band 240.

The body of the retainer 204 can include a longitudinally-extending channel 206 which is configured to receive at least a portion of a medical article. The channel 206 can have a constant or variable cross section, such as a taper, along a portion or all of its length, and can be configured to roughly match the cross section of the portion of the medical article which it is adapted to retain. The channel 206 can extend through an arc of greater than 180 degrees, so as to provide a degree of snap-fit between the retainer 204 and a medical article. The channel 206 has a longitudinal access opening 209 located on the underside of the retainer 204, to allow ingress or egress of a medical article. A medical article can be installed or removed from the underside of the retainer 204 via this access opening 209. Such an arrangement allows a medical provider to align at least a portion of a medical article within the retainer 204 prior to fixing the retainer to the patient's skin. The body of the retainer 204 further includes lateral openings 208a, 208b. The lateral openings 208a, 208b allow ingress and egress of at least a portion of the hinged actuators 216a, 216b into channel 206.

The illustrated retainer 204 includes left and right anchor feet 212a, 212b disposed on anchor pads 218a, 218b. The feet 212a, 212b may be disposed at a position lower than the access opening 209, so as to limit or prevent contact of the retained portion of the medical article with the skin of the patient. The feet 212a, 212b are spaced apart so as to allow ingress and egress of a medical article therebetween. The retainer 204 and the hinged actuators 216a, 216b can be pivotally connected. Each hinged actuator 216a, 216b may pivot around pins 214a, 214b extending from the left and right anchor feet 212a, 212b. Hinged actuators 216a, 216b include engagement members 210a, 210b. In one embodiment the engagement members 210a, 210b include a plurality of spikes. In another embodiment, each engagement member 210a, 210b includes one spike, point, barb, or combination thereof. In some embodiments, the engagement members 210a, 210b are configured to arrest transverse, lateral, and/or longitudinal movement of a medical article positioned within channel 206.

Pins 214a, 214b extend in a transverse direction from the left and right anchor feet 212a, 212b. The hinged actuators 216a, 216b may be manipulated around pins 214a, 214b by the movement of the actuators 216a, 216b. According to one embodiment, movement of the actuators 216a, 216b pivots the actuators around pins 211a, 211b and into and out of lateral openings 208a, 208b. In another embodiment, movement of the actuators 216a, 216b pivots engagement members 210a, 210b into and out of the lateral openings 208a, 208b to engage a medical article.

In some embodiments, left and right anchor feet 212a, 212b include actuator stops 220a, 220b. The actuator stops 220a, 220b may limit the movement of left and right hinged actuators 216a, 216b around left and right pins 214a, 214b. The anchor feet 212a, 212b can have adhesive pads 218a, 218b disposed on the undersides so as to allow attachment of the feet 212a, 212b to the skin of a patient.

Figure 25:
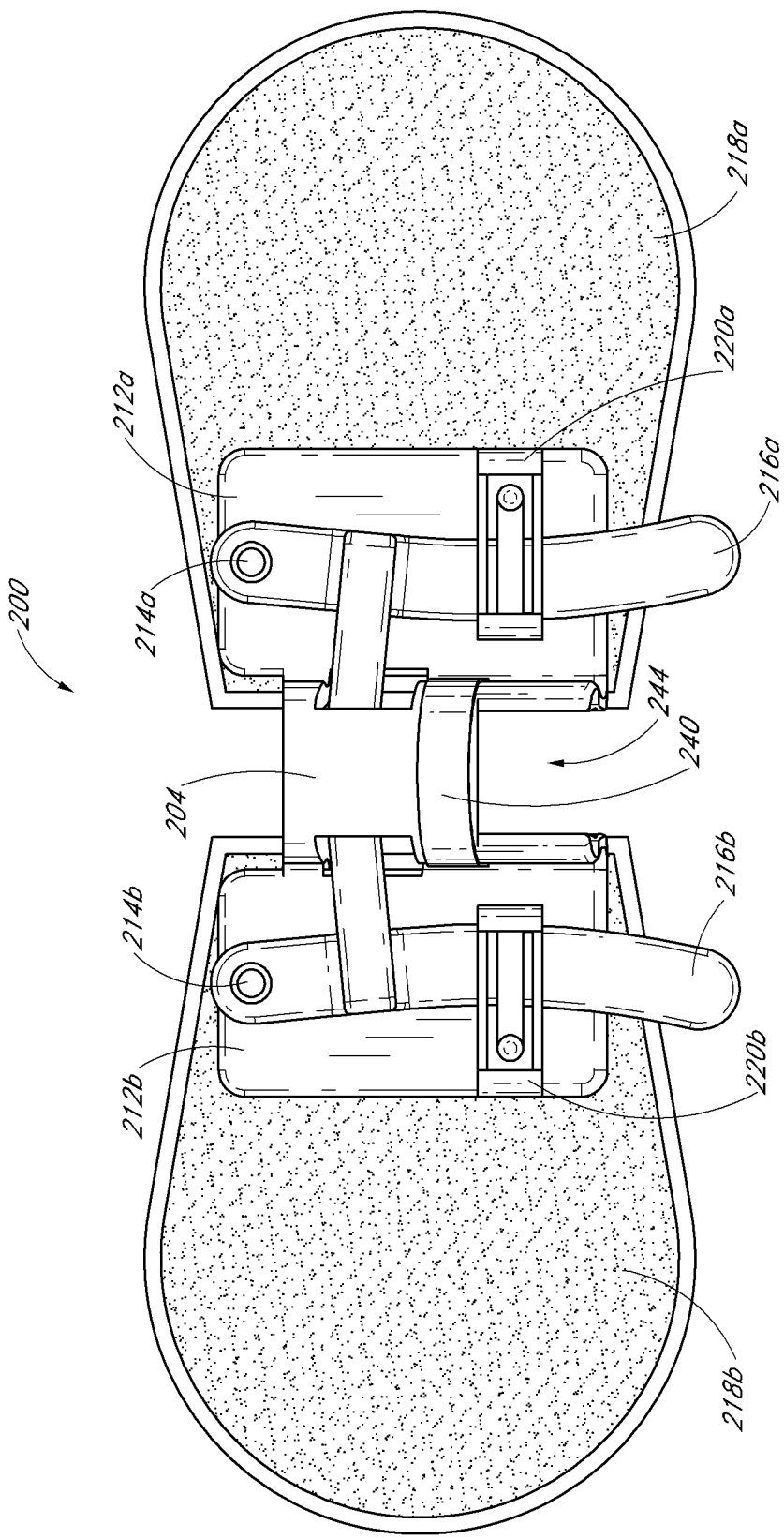
FIG. 25 is a top view of the securement system shown in FIG. 24. The pads shown in FIGS. 24 and 25 are omitted from some of the figures described below to more clearly illustrate the other components of the securement system.
Figure 26:
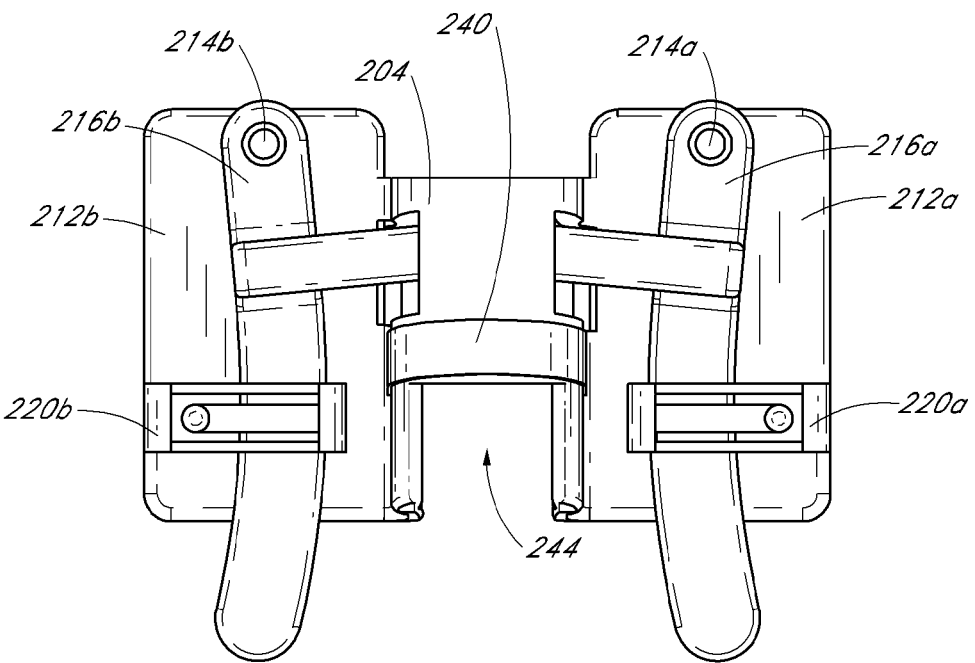
FIG. 26 is a top view of the securement system shown in FIG. 24.
Figure 27:
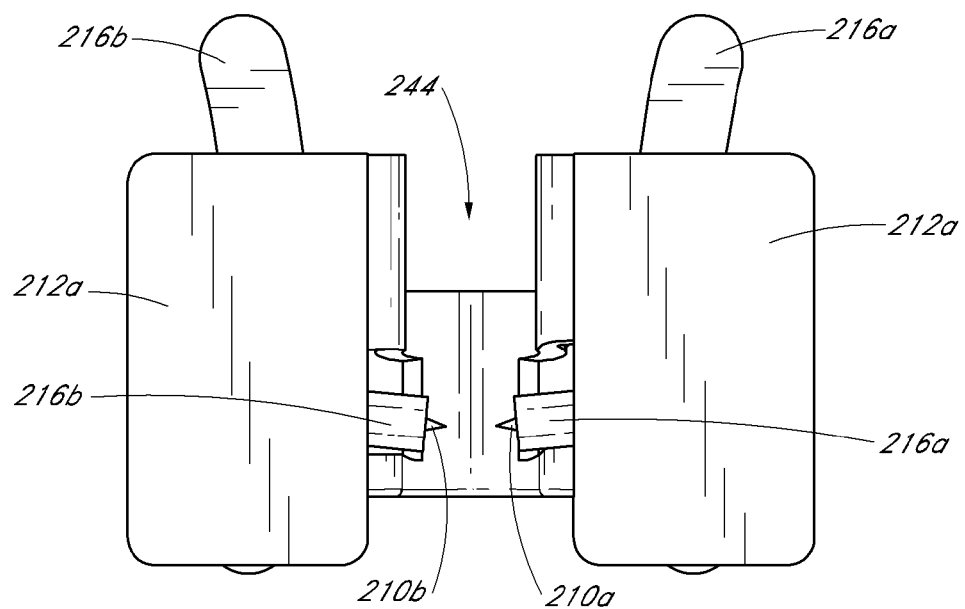
FIG. 27 is a bottom view of the securement system shown in FIG. 24.

FIGS. 25 and 26 are top views of the securement system 200 with and without the anchor pads 218a, 218b shown. FIG. 27 is a bottom view of the securement system 200 without the anchor pads shown. As can be seen in FIG. 27, the engagement members 210a, 210b may extend from the hinged actuators 216a, 216b such that manipulation of the actuators 216a, 216b may pivot the engagement members 210a, 210b.

Figure 28:
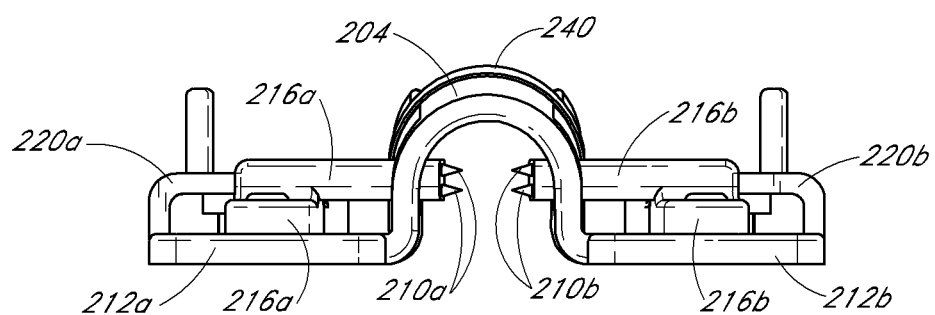
FIG. 28 is a front view of the securement system shown in FIG. 24.
Figure 29:
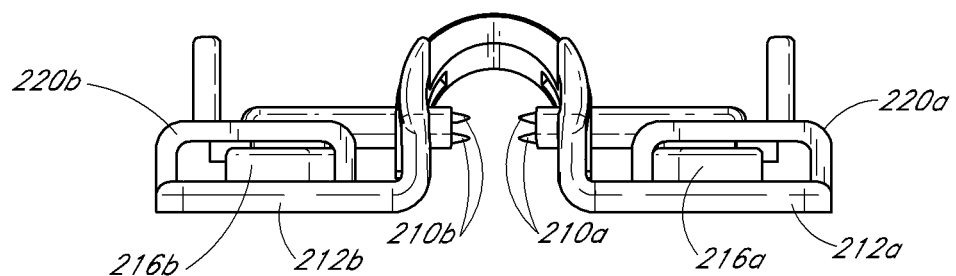
FIG. 29 is a rear view of the securement system shown in FIG. 24.

FIGS. 28 and 29 are front and rear views, respectively, of the securement system 200 shown without anchor pads. As shown in FIGS. 28 and 29, the engagement members 210a, 210b may include a plurality of spikes or points configured to engage a medical article.

Figure 30:
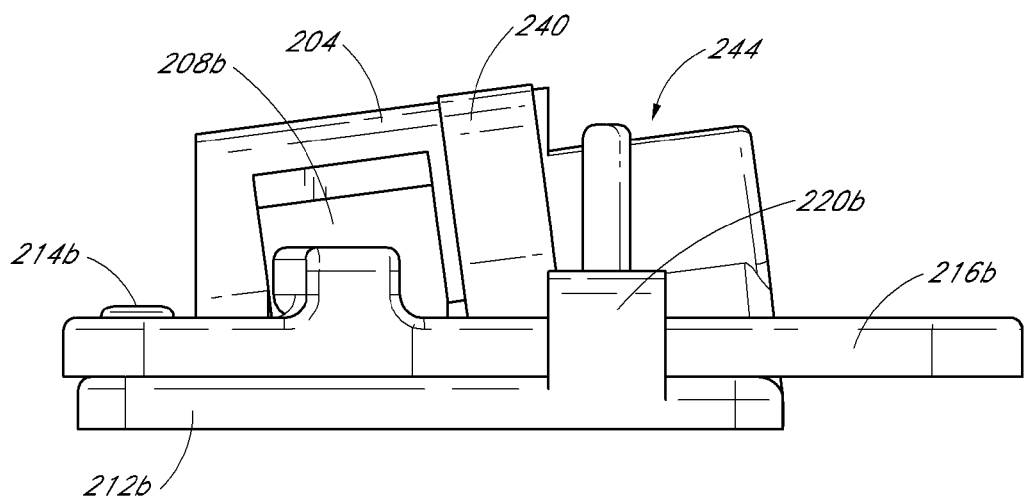
FIGS. 30 and 31 are side views the securement system shown in FIG. 24.
Figure 31:
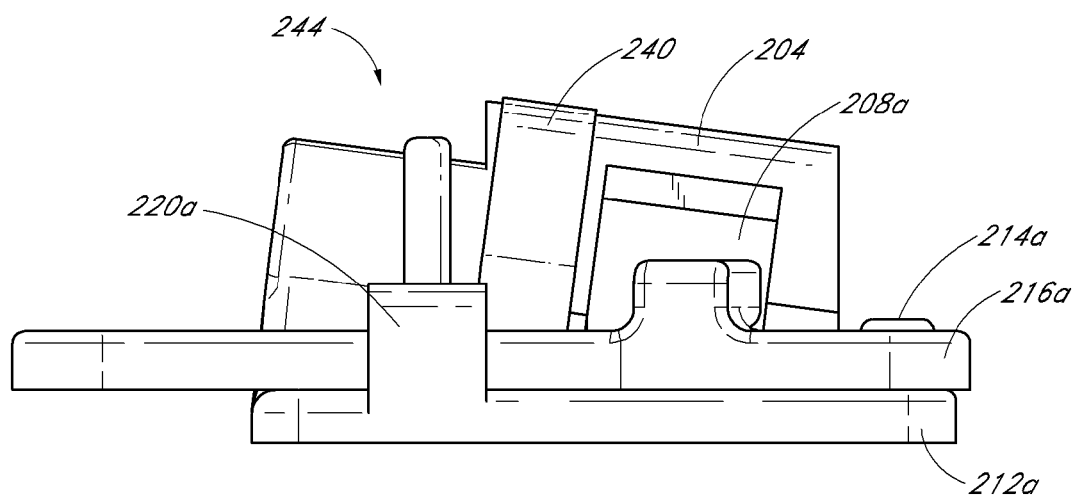

FIGS. 30 and 31 are left and right side views, respectively, of the securement system 200 shown without anchor pads. As can be seen by FIGS. 30 and 31, the retainer 204 may be angled relative to the anchor feet 212a, 212b to provide a desired insertion angle for a medical article.

Figure 32:
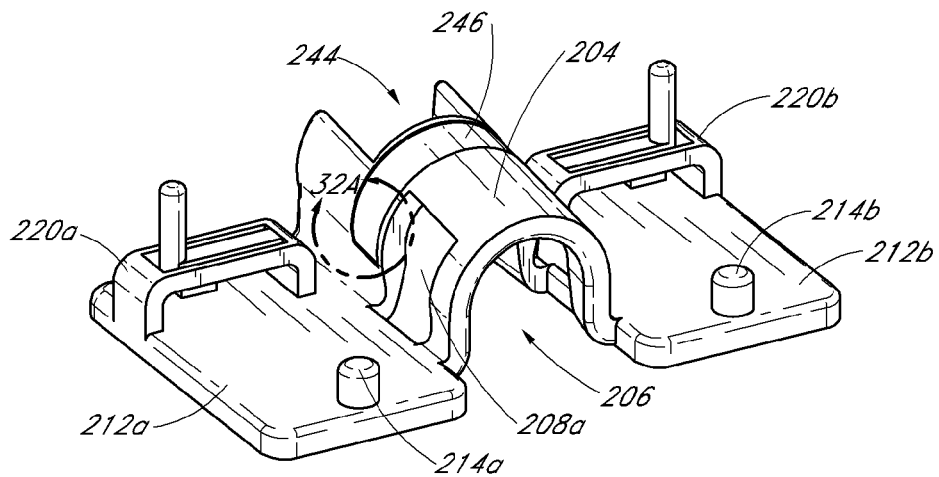
FIG. 32 is a perspective view of the retainer shown in FIGS. 24-31 shown without hinged actuators and a securement band.
Figure 32A:
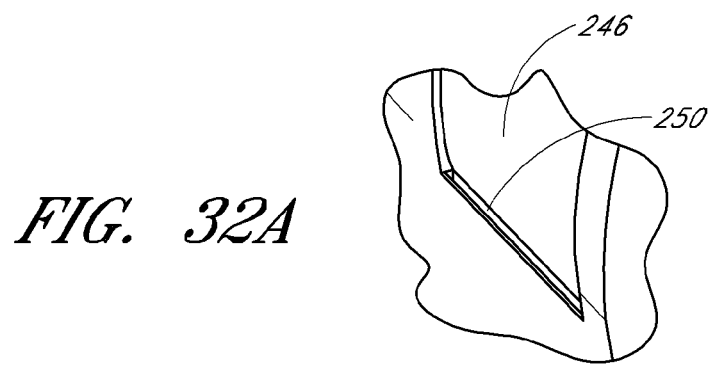
FIG. 32A is an enlarged view of a section of FIG. 32.
Figure 33:
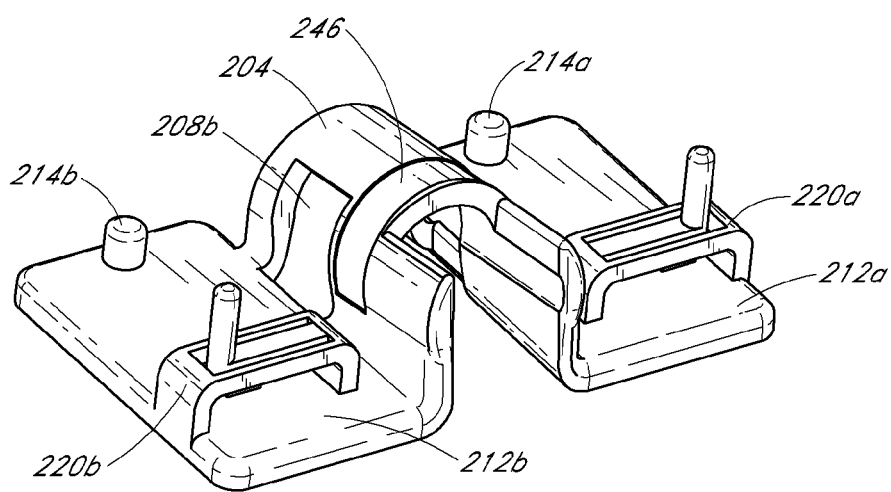
FIG. 33 is a top and rear perspective view of the retainer shown in FIG. 32.

FIGS. 32 and 33 show front and rear perspective views, respectively, of the retainer 204 shown without anchor pads, hinged actuators, or a securement band. FIG. 32A is an enlarged view of a section of FIG. 32 showing a slot 246 and opening 250. Slot 246 provides a guide on retainer 204 for a securement band. A securement band may fit within slot 246 in order to grip or compress retainer 204 or to help maintain the shape of retainer 204. The ends of a securement band may be received by openings 250 in the retainer 204. A medical provider may position a portion of a medical article with channel 206 of retainer 204 and then place a securement band into slot 246 to help the retainer 204 grip the medical article.

Figure 34:
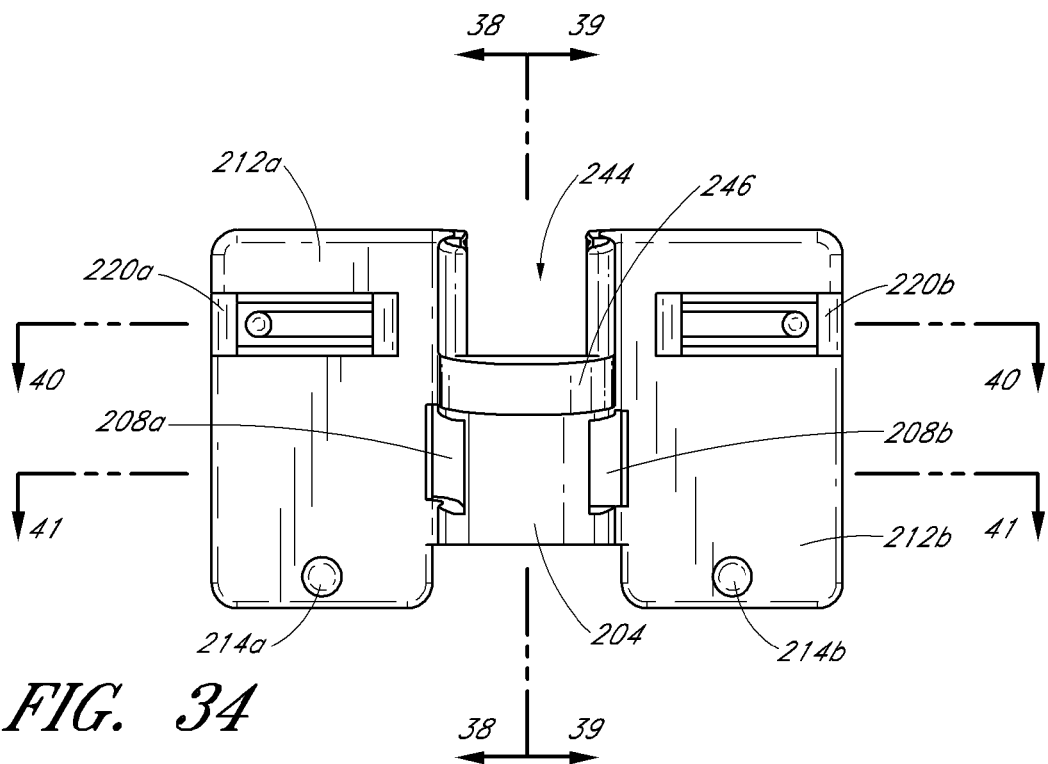
FIG. 34 is a top view of the retainer shown in FIG. 32.
Figure 35:
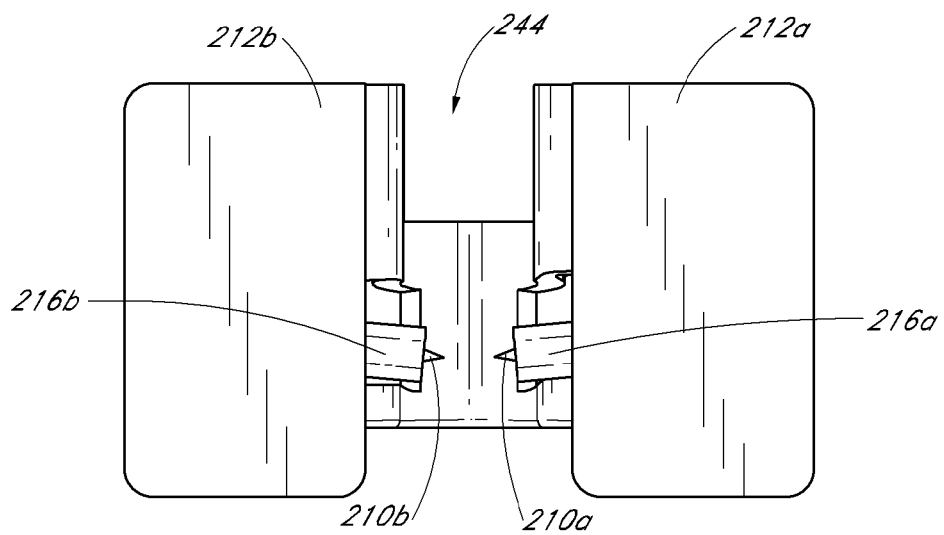
FIG. 35 is a bottom view of the retainer shown in FIG. 32.
Figure 36:
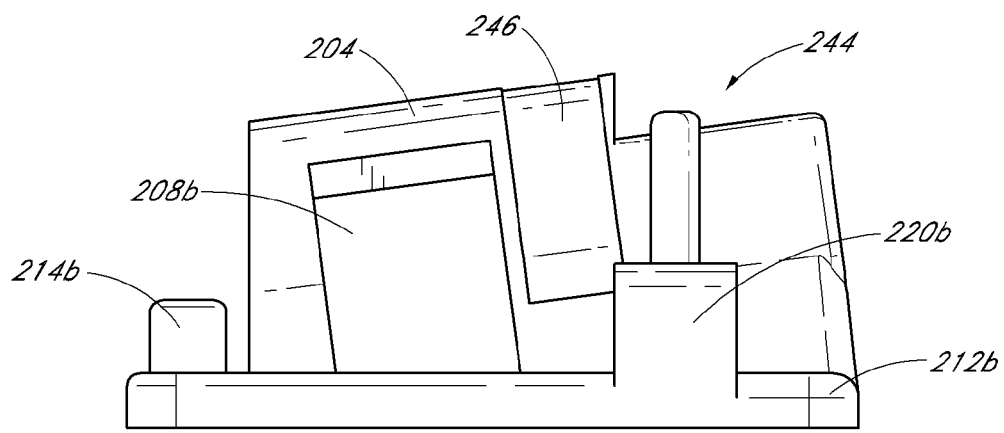
FIGS. 36 and 37 are side views of the retainer shown in FIG. 32.
Figure 37:
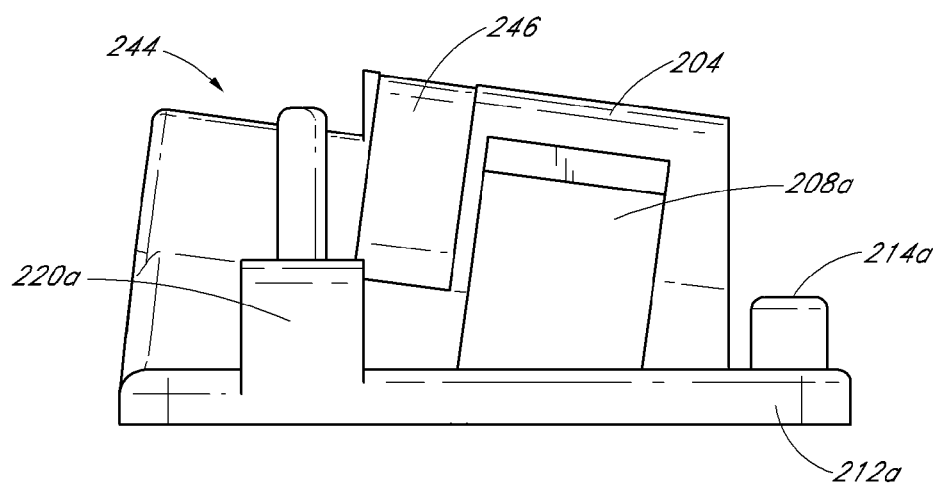
Figure 38:
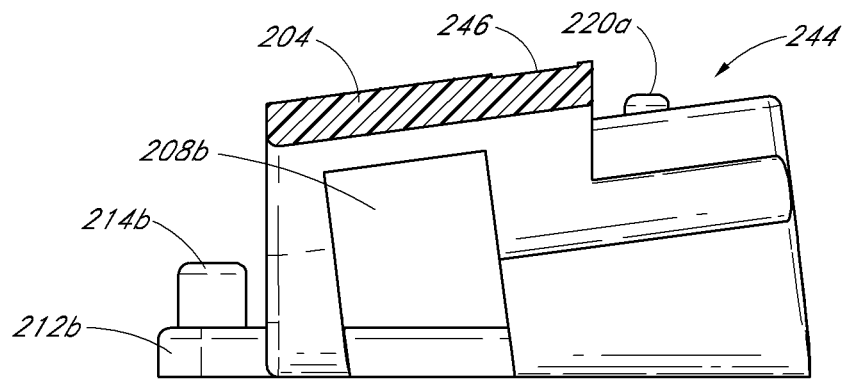
FIG. 38 is a cross-sectional view of the retainer shown in FIG. 34 taken along line 38-38.
Figure 39:
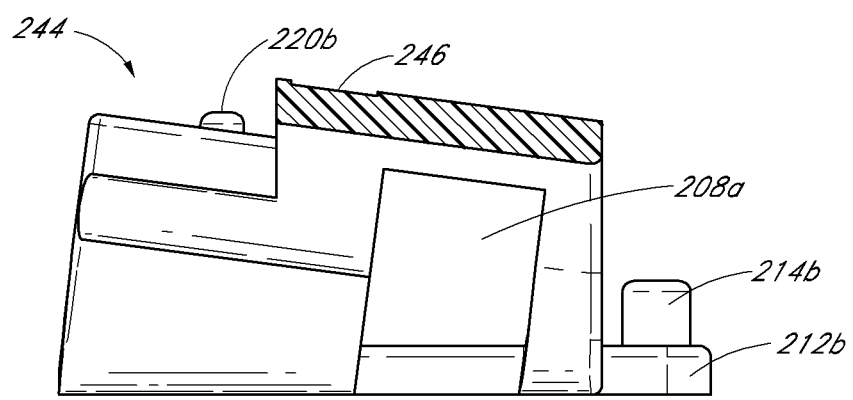
FIG. 39 is a cross-sectional view of the retainer shown in FIG. 34 taken along line 39-39.

FIGS. 34 and 35 show top and bottom views, respectively, of the retainer 204. FIGS. 36 and 37 are right and left side views, respectively, of the securement system 200 shown without anchor pads, hinged actuators, and a securement band. FIGS. 38 and 39 show cross-sectional views of the retainer 204 taken along lines 38-38 and 39-39 respectively. As can be seen in FIGS. 38 and 39, slot 246 may be a subtle depression in retainer 204 to provide a guide for a securement band to be placed on retainer 204.

Figure 40:
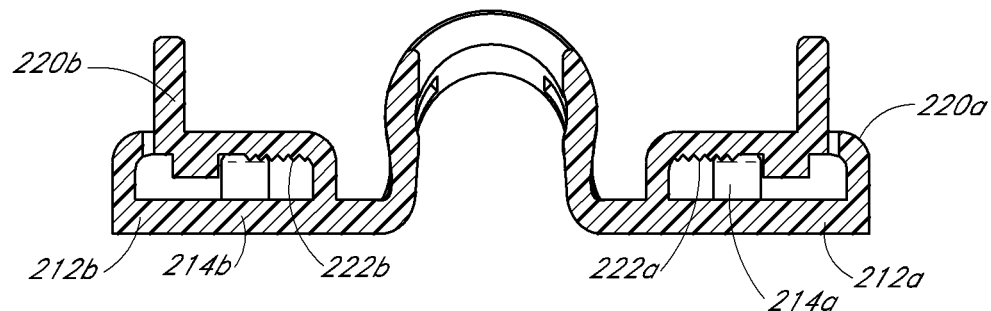
FIG. 40 is a cross-sectional view of the retainer shown in FIG. 34 taken along line 40-40.
Figure 41:
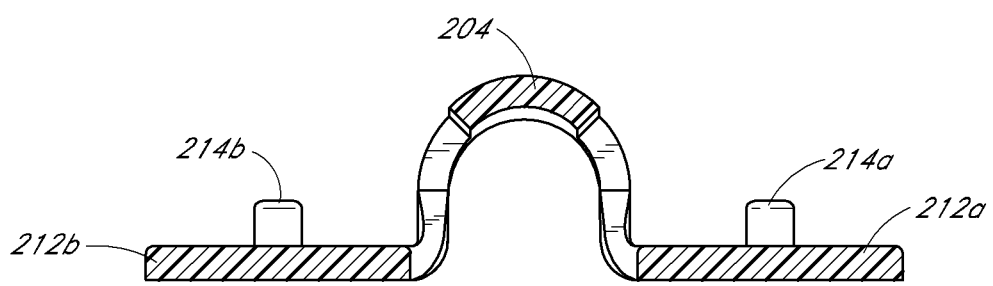
FIG. 41 is a cross-sectional view of the retainer shown in FIG. 34 taken along line 41-41.

FIGS. 40 and 41 are cross-section views of the retainer taken along lines 40-40 and 41-41, respectively. As can be seen in FIG. 40, the underside of actuator stops 220a, 220b may include engagement structure 222a, 222b In some embodiments, the engagement structure 222a, 222b may include teeth and may engage hinged actuators (not shown) in order to adjustably secure the position of the hinged actuators with respect to the retainer 204.

Figure 42:
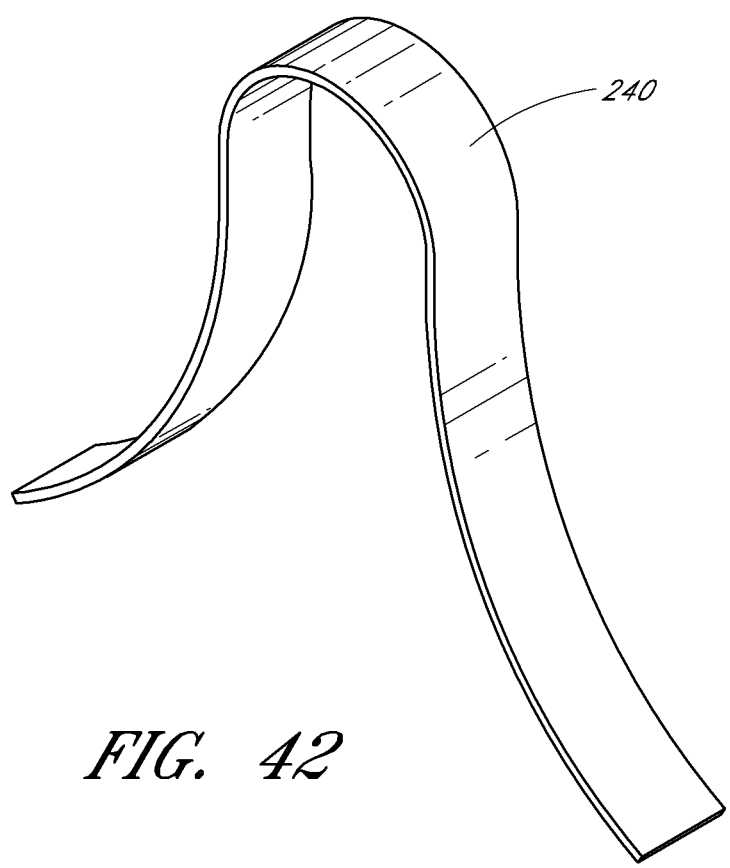
FIG. 42 is a perspective view of a securement band.

FIG. 42 is a perspective view of a securement band 240. The securement band 240 may be placed over a retainer to grip or compress the retainer. The securement 240 band may also be configured to maintain its shape when forces are exerted on the securement band 240. In some embodiments, the securement band 240 may be placed over a retainer to help maintain the shape of the retainer. In some embodiments the securement band 240 comprises metal. In some embodiments the securement band 240 comprises a material with a preformed memory such as a plastic.

Figure 24:
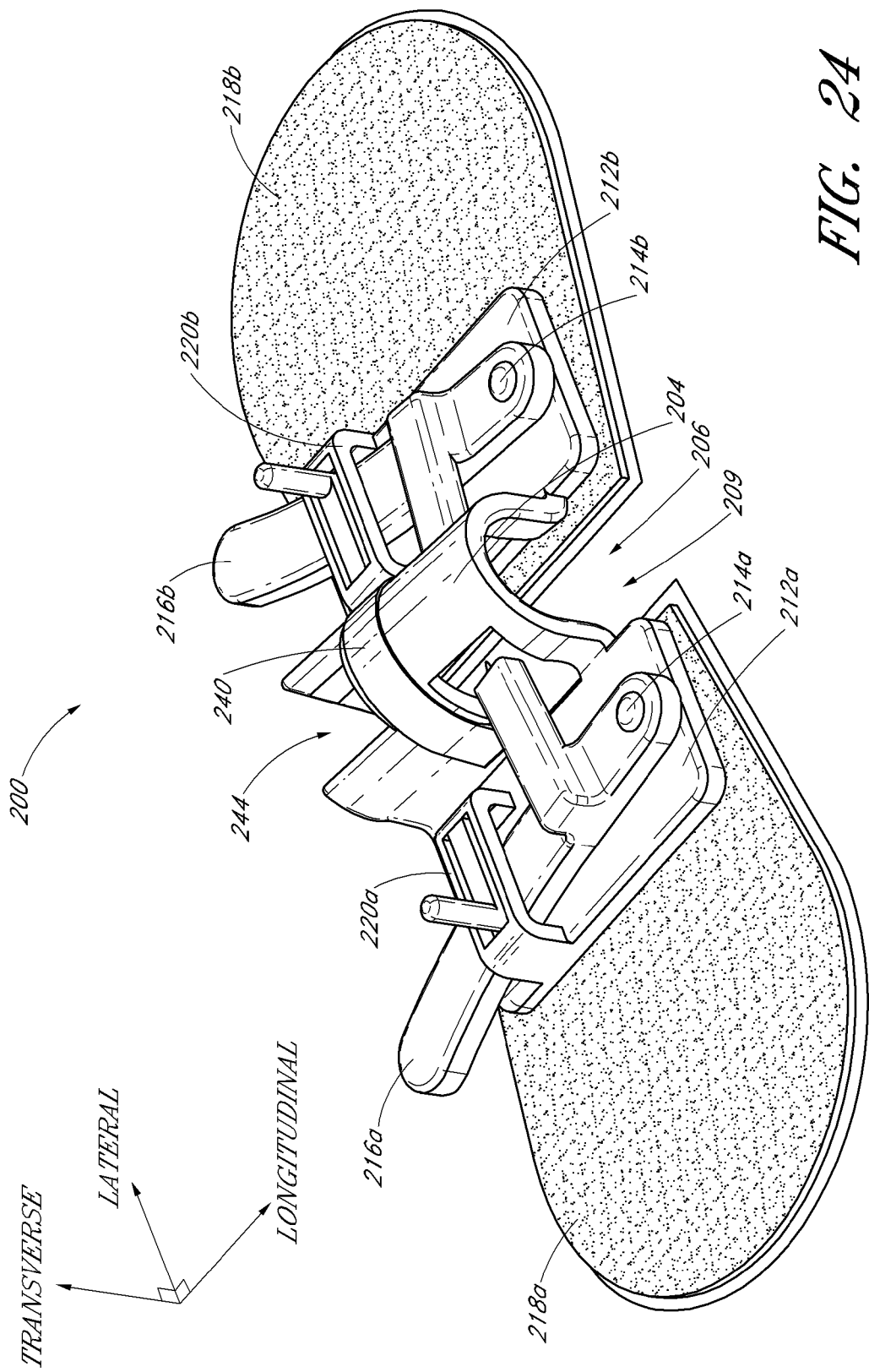
FIG. 24 is a top and front perspective view of another embodiment of a securement system in accordance with an embodiment of the present invention.
Figure 43:
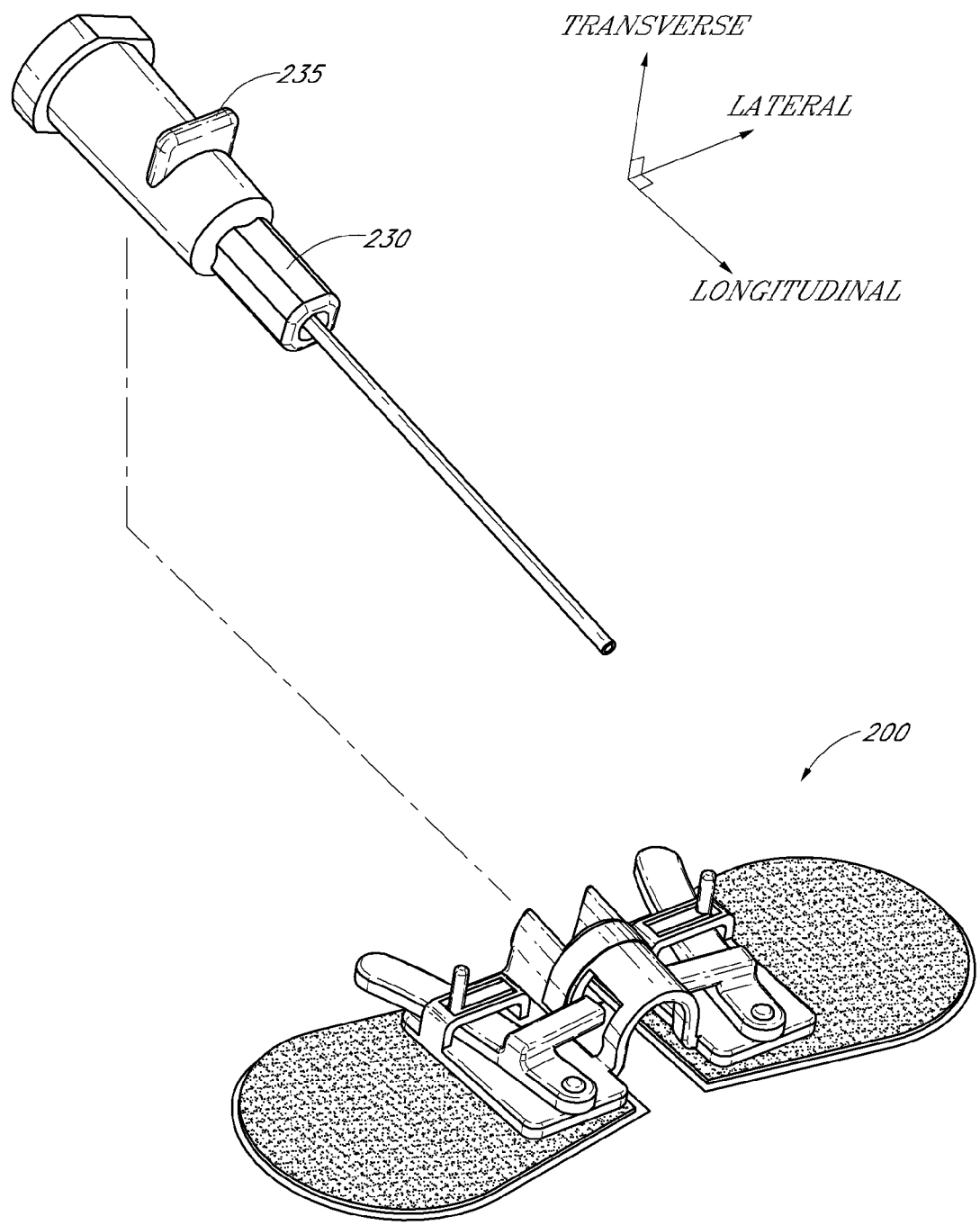
FIG. 43 is a perspective view of the securement system shown in FIG. 24 and a medical article.
Figure 44:
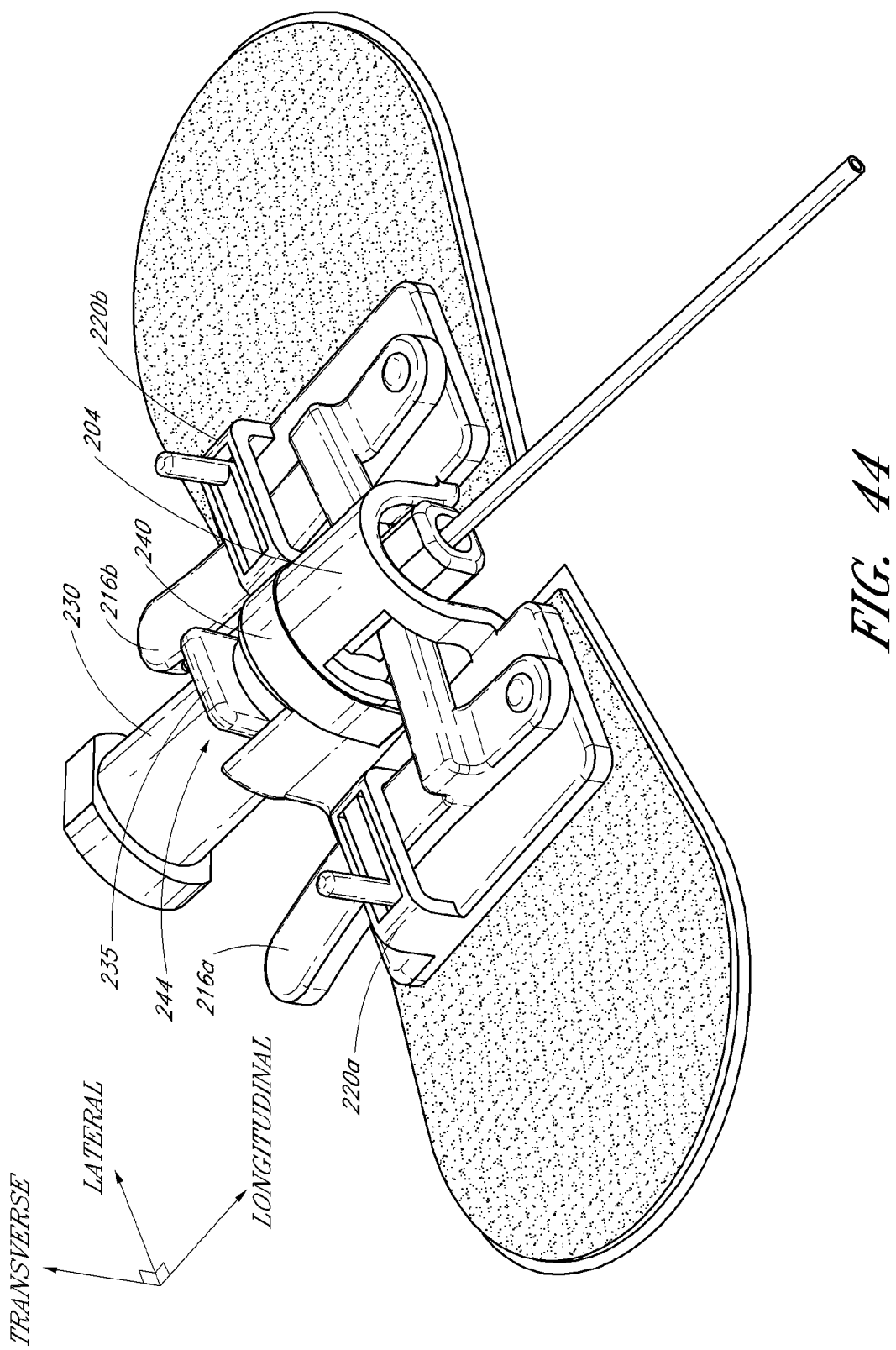
FIG. 44 is a perspective view of the securement system shown in FIG. 24 securing a medical article.

Turning now to FIG. 43, the securement system 200 shown in FIG. 24 is illustrated with a medical article 230. Medical article 230 can include an outwardly extending member or tab 235. In use, a medical professional can secure the medical article 230 relative to a patient's skin using the system 200. As can be seen in FIG. 44, a portion of the medical article 230 is received within the retainer 235 such that the tab 235 is positioned at least partially within the opening 244. In some embodiments, the tab 235 can abut one or more surfaces of the retainer 204 such that longitudinal and/or lateral movement of the medical article 230 relative to the retainer 204 is inhibited. When the medical article 230 is received within the retainer 204, actuators 216a, 216b engage the medical article 230 to inhibit longitudinal, lateral, and transverse movement of the medical article 230 relative to the retainer 204. The actuator stops 220a, 220b limit the movement of the actuators 216a, 216b between at least an open position and a closed position. As discussed above, securement band 240 can be configured to grip the retainer 204 and maintain the shape of the retainer when a portion of the medical article 230 is received therein.

The various embodiments of securement systems described above thus provide a number of ways to provide safe and stable securement for medical articles to the skin of a patient. In addition, the systems described may be broadly applied for use with a variety of medical lines and medical procedures.

Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and systems have been disclosed in the context of certain embodiments and examples, it will be understood by those skilled in the art that these techniques and systems may be extended beyond the specifically disclosed embodiments to other embodiments and/or uses and obvious modifications and equivalents thereof. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein disclosed should not be limited by the particular disclosed embodiments described above but by a fair reading of the claims that follow.

What is claimed is:

1. A retainer comprising:
 a body member having a channel and one or more openings, the channel having a longitudinal axis and receiving at least a portion of a medical article, the one or more openings being disposed in the body member;
 one or more base portions coupled with the body member and extending laterally from the body member, the one or more base portions supporting the body member; and
 one or more actuators being movably coupled with the one or more base portions so as to move between a first position and a second position, at least a portion of each actuator being disposed in the channel when the actuator is in the first position and removed from the channel when the actuator is in the second position.

2. The retainer of claim 1 further comprising one or more pins, at least one of the one or more actuators pivoting around the one or more pins when moving to the first position.

3. The retainer of claim 2, wherein the pin extends in a generally transverse direction from the one or more base portions.

4. The retainer of claim 1, wherein each of the one or more actuators has a length in the longitudinal direction that is greater than a length in the longitudinal direction of the one or more base portions.

5. The retainer of claim 1 further comprising one or more actuator stops, each actuator stop inhibiting movement of the one or more actuators from moving to the second position.

6. The retainer of claim 5, wherein the one or more actuator stops are selectably engageable with the one or more actuators to allow the one or more actuators to move to the second position.

7. The retainer of claim 1, wherein the one or more openings are disposed so that the portion of each actuator passes through the one or more openings when the actuator moves to the first position.

8. The retainer of claim 1 further comprising at least one opening capable of receiving an outwardly extending member of the medical article.

9. The retainer of claim 1, wherein the channel is tapered in the longitudinal direction.

10. The retainer of claim 1 further comprising one or more abutment surfaces, the abutment surfaces being configured to contact the medical article and to inhibit longitudinal movement of the secured medical article relative to the retainer.

11. The retainer of claim 1, wherein the body member comprises a lower opening to allow at least ingress of a medical article into the channel.

12. The retainer of claim 1, wherein the portion of each actuator disposed within the channel comprises at least one engagement member, the engagement member contacting the medical article at least when the actuator is in the first position.

13. The retainer of claim 12, wherein the engagement member comprises a spike.

14. A retainer for securing a medical article relative to a patient, the retainer comprising:
a body member forming a channel and having a first opening in a lateral side of the body member, the channel having a longitudinal axis and being configured to receive at least a portion of the medical article with at least a portion of the medical article being aligned with the first opening;
a first base portion coupled with the body member and extending laterally from the body member at a location below the longitudinal axis of the channel; and
a first actuator movably coupled with the first base portion, the first actuator moving relative to the body member between at least a first position and a second position, at least a portion of the first actuator being received within the first opening when the first actuator is in the first position.

15. The retainer of claim 14, wherein the first base portion comprises a pin and the first actuator is configured to rotate about the pin.

16. The retainer of claim 14, wherein the body member comprises a second opening on a lateral side of the body member, and the first opening is juxtaposed relative to the second opening.

17. The retainer of claim 14 further comprising a second base portion coupled with the body member and a second actuator coupled with the second base portion, the second actuator being configured to move relative to the body member between at least a first position and a second position.

18. The retainer of claim 14 further comprising a band disposed over at least a portion of the body member, the band maintaining the shape of the body member when at least a portion of the medical article is received within the channel.

19. A retainer for securing a medical article relative to a patient, the retainer comprising: a body member forming a channel having a longitudinal axis, the longitudinal axis extending beyond both ends of the channel, the channel being configured to receive at least a portion of the medical article; a base portion coupled with the body member and extending laterally from the body member at a location below the longitudinal axis of the channel, wherein a plane defined by the base portion does not intersect the longitudinal axis at least at a location below the body member; an actuator movably coupled with the base portion, the actuator moving relative to the body member between at least a first position and a second position; and an actuator stop coupled with the base portion and selectively limiting movement of the actuator relative to the body member and toward the second position, at least a portion of the actuator stop being movable so as to allow the actuator to move to the second position.

20. The retainer of claim 19, wherein the actuator stop comprises engagement structure configured to engage the actuator as the actuator is moved between the first position and the second position.

21. The retainer of claim 20, wherein the engagement structure comprises teeth configured to releasably secure the position of the actuator with respect to the body member.

* * * * *